US012740993B2

(12) United States Patent
Meiri et al.

(10) Patent No.: US 12,740,993 B2
(45) Date of Patent: Sep. 22, 2026

(54) CANNABINOIDS AND USES THEREOF FOR TREATMENT OF ESTROGEN RECEPTOR RELATED DISEASES

(71) Applicant: TECHNION RESEARCH AND DEVELOPMENT FOUNDATION LIMITED, Haifa (IL)

(72) Inventors: David Meiri, Haifa (IL); Vered Cohen, Haifa (IL)

(73) Assignee: TECHNION RESEARCH AND DEVELOPMENT FOUNDATION LIMITED, Haifa (IL)

( * ) Notice: Subject to any disclaimer, the term of this patent is extended or adjusted under 35 U.S.C. 154(b) by 507 days.

(21) Appl. No.: 18/259,458

(22) PCT Filed: Dec. 27, 2021

(86) PCT No.: PCT/IL2021/051537
§ 371 (c)(1),
(2) Date: Jun. 27, 2023

(87) PCT Pub. No.: WO2022/144878
PCT Pub. Date: Jul. 7, 2022

(65) Prior Publication Data
US 2024/0075046 A1 Mar. 7, 2024

Related U.S. Application Data

(60) Provisional application No. 63/131,075, filed on Dec. 28, 2020.

(51) Int. Cl.
*A61K 31/00* (2006.01)
*A61K 31/135* (2006.01)
*A61P 15/00* (2006.01)
*A61P 35/00* (2006.01)

(52) U.S. Cl.
CPC .......... *A61K 31/658* (2023.05); *A61K 31/135* (2013.01); *A61P 15/00* (2018.01); *A61P 35/00* (2018.01)

(58) Field of Classification Search
CPC ..... A61K 31/658; A61K 31/135; A61P 15/00; A61P 35/00
See application file for complete search history.

(56) References Cited

U.S. PATENT DOCUMENTS

| | | | |
|---|---|---|---|
| 4,235,871 A | 11/1980 | Papahadjopoulos | |
| 4,501,728 A | 2/1985 | Geho | |
| 4,666,828 A | 5/1987 | Gusella | |
| 4,683,202 A | 7/1987 | Mullis | |
| 4,801,531 A | 1/1989 | Frossard | |
| 4,837,028 A | 6/1989 | Allen | |
| 5,019,369 A | 5/1991 | Presant | |
| 5,192,659 A | 3/1993 | Simons | |
| 5,272,057 A | 12/1993 | Smulson | |
| 2020/0179330 A1 | 6/2020 | Heaney | |
| 2025/0387417 A1* | 12/2025 | Mandel | A61K 31/658 |

FOREIGN PATENT DOCUMENTS

WO 2020160452 A1 8/2020

OTHER PUBLICATIONS

Turner et al. (Turner) (Turner, C. E. Constituents of *Cannabis sativa* L. XVII. A Review of the Natural Constituents. Journal of Natural Products 1980, 43, 169-234. (Year: 1980).*

Peng, Y. et al. HPLC analysis, semi-preparative HPLC preparation and identification of three impurities in salidroside bulk drug. J. Pharm. Biomed. Anal. 2009, 49, 828-832. (Year: 2009).*

Zheng, Z. et al. Semi-Preparative Separation of 10 Caffeoylquinic Acid Derivatives Using High Speed Counter-Current Chromatogaphy Combined with Semi-Preparative HPLC from the Roots of Burdock (*Arctium lappa* L.). Molecules 2018, 23, 429. (Year: 2018).*

Aravind, S. G. et al. Semi-preparative HPLC preparation and HPTLC quantification of tetrahydroamentoflavone as marker in Semecarpus anacardium and its polyherbal formulations. Journal of Pharmaceutical and Biomedical Analysis 2008, 48, 808-813. (Year: 2008).*

Ben-Shabat et al., (1998) An entourage effect: inactive endogenous fatty acid glycerol esters enhance 2-arachidonoyl-glycerol cannabinoid activity. European Journal of Pharmacology 353(1): 23-31.

Buchwald et al., (1980) Long-term, continuous intravenous heparin administration by an implantable infusion pump in ambulatory patients with recurrent venous thrombosis. Surgery 88(4): 507-516.

Dobovišek et al., (2020) Cannabinoids and Hormone Receptor-Positive Breast Cancer Treatment. Cancers (Basel) 12(3): 525, 12 pages.

(Continued)

*Primary Examiner* — Jeffrey H Murray
*Assistant Examiner* — Kristen W Romero
(74) *Attorney, Agent, or Firm* — Fuller IP Law LLC; Rodney J. Fuller

(57) ABSTRACT

The present invention provides a pharmaceutical composition comprising one or more cannabinoids, wherein one of the cannabinoids is a compound having a structure represented by Formula II:

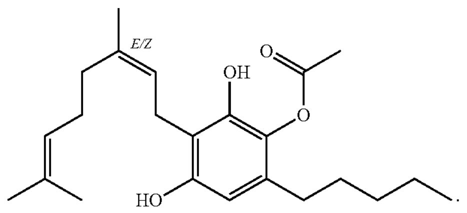

The present invention also provides a method for treating a subject afflicted with an estrogen receptor-related diseases comprising administering to the subject the pharmaceutical composition comprising the compound of Formula II. The present invention further provides a combination therapy comprising one or more cannabinoids, wherein one of the cannabinoids is the compound of Formula II, and an estrogen receptor activation inhibitor and use thereof in sensitizing subjects that are resistant to treatment with the estrogen receptor activation inhibitor alone.

20 Claims, 25 Drawing Sheets

(56) References Cited

OTHER PUBLICATIONS

Langer (1990) New methods of drug delivery. Science 249(4976): 1527-1533.
McPartland and Russo (2001) Cannabis and Cannabis Extracts: Greater Than the Sum of Their Parts? Journal of Cannabis Therapeutics 1(3-4): 103-132.
Saudek et al., (1989) A preliminary trial of the programmable implantable medication system for insulin delivery. N Engl J Med 321(9): 574-579.
Sefton (1987) Implantable pumps. Crit Rev Biomed Eng 14(3): 201-240.
Blasco-Benito et al., (2018) Appraising the "entourage effect": Antitumor action of a pure cannabinoid versus a botanical drug preparation in preclinical models of breast cancer. Biochem Pharmacol 157: 285-293.

* cited by examiner

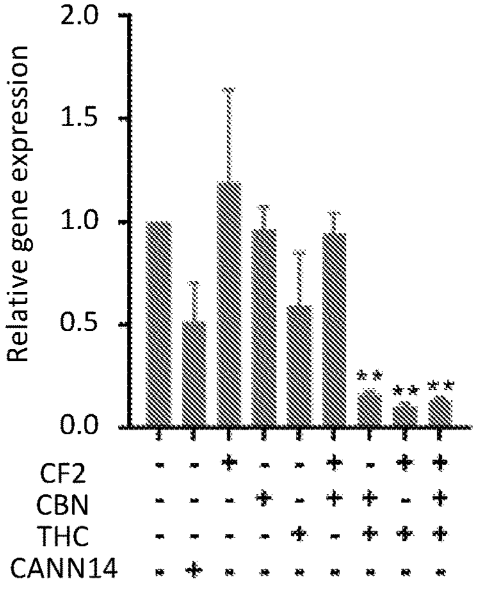
Figure 7C
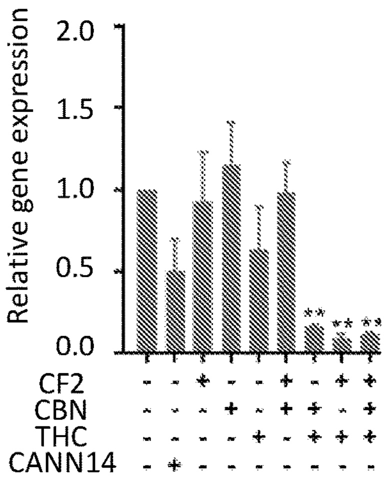
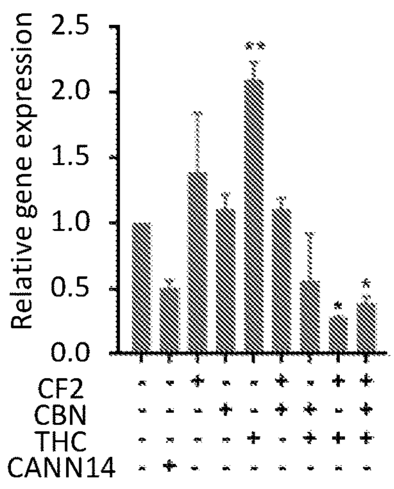
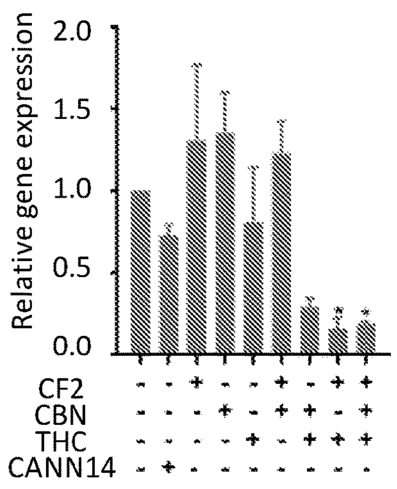
Figure 7D Figure 7E Figure 7F

CANNABINOIDS AND USES THEREOF FOR TREATMENT OF ESTROGEN RECEPTOR RELATED DISEASES

CROSS-REFERENCE TO RELATED APPLICATIONS

This application is the U.S. National Stage of International Patent Application No. PCT/IL2021/051537, filed on Dec. 27, 2021, which claims the benefit of and priority to U.S. Provisional Patent Application No. 63/131,075, filed on Dec. 28, 2020, the contents of each of which are hereby incorporated by reference in their entireties.

FIELD OF INVENTION

The present invention relates to cannabinoid compounds, pharmaceutical compositions comprising same, and methods of use thereof.

BACKGROUND

Estrogen is a sex hormone that plays a key role in the development and regulation of the female reproductive system. In normal cells, estrogen binds either estrogen receptor alpha or beta (ERα or ERβ), leading to ligand-activated signaling. In the absence of estrogen, the estrogen receptors remain in an inactive form. However, in the presence of estrogen, the receptors undergo a conformational change and form a dimerization complex that is translocated to the nucleus. In ER-related diseases including cancer, estrogen stimulates cell growth and further development by enhancing expression of genes related to cell proliferation and survival.

Accordingly, the predominant treatment strategy of ER-related diseases aims at inhibiting ERα activation by multiple inhibitors (endocrine therapy). These inhibitors are divided into three categories based on their mechanism of action: (i) Aromatase Inhibitors (AIs) that inhibit estradiol biosynthesis; (ii) Selective Estrogen Receptor Degraders (SERDs) that bind to ERα causing its degradation; and (iii) Selective Estrogen Receptor Modulators (SERMs) that function as antagonists by competing with estradiol for binding.

There are several types of SERMs, the most prominent one being tamoxifen, which was listed by the World Health Organization as an essential drug for breast cancer treatment. Tamoxifen is also being used for the prevention of cancer in women at high risk of developing breast cancer. Following surgery for tumor removal, breast cancer patients are required to complete daily tamoxifen treatment for at least 5 years. However, there is known to be poor adherence to tamoxifen treatment predominantly due to adverse effects which include hot flashes, pain, nausea, fatigue, constipation, loss of libido, weight gain, vaginal dryness, abnormal discharge and bleeding, and mental issues such as depression, irritability, and negative mood. Patients younger than 50 or that were pre-treated with hormonal therapy are more likely to report severe adverse effects.

The *Cannabis* plant is being used as a supplement in therapy of numerous diseases and conditions including cancer, primarily as palliative care to alleviate pain, stimulate appetite while preventing nausea and vomiting. It includes more than 120 different phytocannabinoids which represent a group of C21 or C22 (for the carboxylated forms) terpenophenolic compounds that are generally categorized into 10 subclasses. The predominant phytocannabinoid compounds found in *Cannabis* are tetrahydrocannabinolic acid (THCA), cannabidiolic acid (CBDA), and cannabinolic acid (CBNA), followed by cannabigerolic acid (CBGA), cannabichromenic acid (CBCA), and cannabinodiolic acid (CBNDA). Most of the biological properties related to cannabinoids rely on their interactions with the endocannabinoid system in humans. The endocannabinoid system mainly includes two G protein-coupled cannabinoid receptors, CB1 and CB2, as well as two endogenous ligands, anandamide (AEA) and 2-arachidonylglycerol (2-AG).

While single cannabinoids have been shown to exert biological activity, *Cannabis* synergy, also known as the "entourage effect", in which a variety of "minor cannabinoids" markedly increase the activity of the primary endogenous cannabinoids has long been recognized (Ben-Shabat et al., 1998, Eur. J. Pharmacol. 353:23-31, McPartland, 2001, J. *Cannabis* Ther. 1:103-132). These so-called minor phytocannabinoids and other compounds in *Cannabis* such as terpenoids and flavonoids have been poorly studied for their potential therapeutic effects.

There is a great unmet need for pharmaceutical compositions suitable for treating diseases related to ER. Furthermore, there is a great unmet need for compositions and methods for sensitizing subjects which are resistant to currently available ER activation inhibitors.

SUMMARY

The present invention provides a pharmaceutical cannabinoid composition comprising a compound having a structure represented by Formula II:

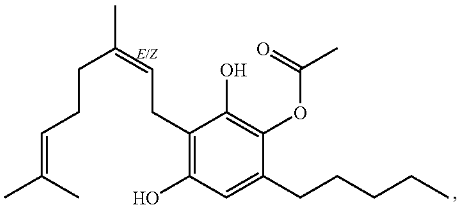

or a pharmaceutically acceptable salt thereof. The present invention further provides methods of use of said compound or salt or a pharmaceutical composition comprising same for the treatment of a disease related to estrogen receptor (ER) as well as for increasing the sensitivity of a subject afflicted with an ER-related disease to an ER activation inhibitor.

The present invention is based, in part, on the unexpected finding that a composition comprising the compound of the invention was highly potent in inducing cell death of different types of tumor cells. Further, the present invention is based, in part, on the surprising finding that a combination of the pharmaceutical composition of the invention and an ER activation inhibitor, e.g., tamoxifen, increased apoptosis % of cancer cells by more than 40%, compared to tamoxifen alone.

According to a first aspect, there is provided a pharmaceutical cannabinoid composition comprising a compound having a structure represented by Formula II:

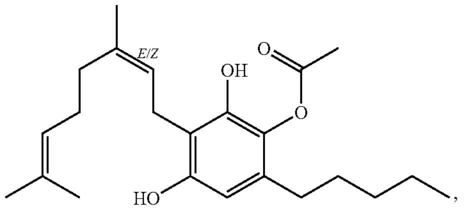

or a pharmaceutically acceptable salt thereof.

According to a second aspect, there is provided a method for treating a subject afflicted with an ER-related disease, the method comprising administering to the subject a therapeutically effective amount of a compound having a structure represented by Formula II or a pharmaceutically acceptable salt thereof or a pharmaceutical composition comprising same, thereby treating the subject afflicted with an ER-related disease.

According to a third aspect, there is provided a method for increasing or enhancing the therapeutic efficacy of an ER activation inhibitor in a subject in need thereof, the method comprising administering to the subject a therapeutically effective amount of a compound having a structure represented by Formula II or a pharmaceutically acceptable salt thereof or a pharmaceutical composition comprising same.

According to another aspect, there is provided a pharmaceutical combination comprising: (a) at least one cannabinoid comprising a compound having a structure represented by Formula II or a pharmaceutically acceptable salt thereof; and (b) at least one ER activation inhibitor.

According to yet another aspect, there is provided a method for treating a subject afflicted with an ER-related disease, the method comprising administering to the subject a therapeutically effective amount of a pharmaceutical combination comprising: (a) at least one cannabinoid comprising a compound having a structure represented by Formula II or a pharmaceutically acceptable salt thereof; and (b) at least one ER activation inhibitor.

According to a further aspect, there is provided a method for sensitizing a subject afflicted with an ER-related disease to an ER activation inhibitor, wherein the subject is resistant or non-responsive to treatment with an ER activation inhibitor alone, the method comprising administering to the subject a therapeutically effective amount of a pharmaceutical combination comprising: (a) at least one cannabinoid comprising a compound having a structure represented by Formula II or a pharmaceutically acceptable salt thereof; and (b) at least one ER activation inhibitor.

In some embodiments, the pharmaceutical cannabinoid composition comprises a compound having a structure represented by Formula II or a pharmaceutically acceptable salt thereof as the sole cannabinoid in said composition.

In some embodiments, the pharmaceutical cannabinoid composition further comprises at least one additional cannabinoid.

In some embodiments, the compound having a structure represented by Formula II or a pharmaceutically acceptable salt thereof constitutes at least 1% by weight of the total cannabinoid content in the composition. In some embodiments, the compound having a structure represented by Formula II or a pharmaceutically acceptable salt thereof constitutes at least 3% by weight of the total cannabinoid content in the composition. In some embodiments, the compound having a structure represented by Formula II or a pharmaceutically acceptable salt thereof constitutes at least 5% by weight of the total cannabinoid content in the composition. In some embodiments, the compound having a structure represented by Formula II or a pharmaceutically acceptable salt thereof constitutes at least 10% by weight of the total cannabinoid content in the composition.

In some embodiments, the pharmaceutical cannabinoid composition further comprises THC ((−)-$\Delta^9$-trans-tetrahydrocannabinol ($\Delta^9$-THC)), CBN (cannabinol), or both.

In some embodiments, one or more of the cannabinoids in the composition is present as a highly purified extract of *Cannabis*.

In some embodiments, one or more of the cannabinoids in the composition is a synthetically produced cannabinoid.

In some embodiments, the pharmaceutical cannabinoid composition comprises a compound having a structure represented by Formula II or a pharmaceutically acceptable salt thereof and THC.

In some embodiments, the pharmaceutical cannabinoid composition comprises a compound having a structure represented by Formula II or a pharmaceutically acceptable salt thereof and THC in a weight per weight (w/w) ratio ranging from 1:10 to 1:1,500, including all iterations of ratios within the specified range. In some embodiments, the pharmaceutical cannabinoid composition comprises a compound having a structure represented by Formula II or a pharmaceutically acceptable salt thereof and THC in a weight per weight (w/w) ratio ranging from 1:1 to 1:1,500, including all iterations of ratios within the specified range. In some embodiments, the pharmaceutical cannabinoid composition comprises a compound having a structure represented by Formula II or a pharmaceutically acceptable salt thereof and THC in a weight per weight (w/w) ratio ranging from 1,500:1 to 1:1, including all iterations of ratios within the specified range.

In some embodiments, the pharmaceutical cannabinoid composition comprises a compound having a structure represented by Formula II or a pharmaceutically acceptable salt thereof and CBN.

In some embodiments, the pharmaceutical cannabinoid composition comprises a compound having a structure represented by Formula II or a pharmaceutically acceptable salt thereof and CBN in a weight per weight (w/w) ratio ranging from 1:1 to 1:40, including all iterations of ratios within the specified range. In some embodiments, the pharmaceutical cannabinoid composition comprises a compound having a structure represented by Formula II or a pharmaceutically acceptable salt thereof and CBN in a weight per weight (w/w) ratio ranging from 1:1 to 1:100, including all iterations of ratios within the specified range. In some embodiments, the pharmaceutical cannabinoid composition comprises a compound having a structure represented by Formula II or a pharmaceutically acceptable salt thereof and CBN in a weight per weight (w/w) ratio ranging from 100:1 to 1:1, including all iterations of ratios within the specified range.

In some embodiments, the pharmaceutical cannabinoid composition comprises a compound having a structure represented by Formula II or a pharmaceutically acceptable salt thereof, CBN, and THC.

In some embodiments, the pharmaceutical cannabinoid composition comprises a compound having a structure represented by Formula II or a pharmaceutically acceptable salt thereof, CBN, and THC, wherein CBN and THC are present in the composition in a weight per weight (w/w) ratio ranging from 1:5 to 1:100, including all iterations of ratios within the specified range. In some embodiments, the pharmaceutical cannabinoid composition comprises a compound having a structure represented by Formula II or a pharmaceutically acceptable salt thereof, CBN, and THC, wherein CBN and THC are present in the composition in a weight per weight (w/w) ratio ranging from 1:1 to 1:1,000, including all iterations of ratios within the specified range. In some embodiments, the pharmaceutical cannabinoid composition comprises a compound having a structure represented by Formula II or a pharmaceutically acceptable salt thereof, CBN, and THC, wherein CBN and THC are present in the composition in a weight per weight (w/w) ratio ranging from 1,000:1 to 1:1, including all iterations of ratios within the specified range.

In some embodiments, the pharmaceutical cannabinoid composition comprises a compound having a structure represented by Formula II or a pharmaceutically acceptable salt thereof, CBN, and THC in a weight per weight (w/w) ratio ranging from 1:1:10 to 1:30:1,500, including all iterations of ratios within the specified range.

In some embodiments, the pharmaceutical cannabinoid composition is used in the treatment of a subject afflicted with an estrogen receptor (ER)-related disease.

In some embodiments, the ER-related disease comprises a cell-proliferation related disease.

In some embodiments, the ER-related disease is selected from the group consisting of: breast cancer, ovarian cancer, colon cancer, endometrial cancer, endometriosis, fibrosis, dysmenorrhea, and gynecomastia. Each possibility represents a separate embodiment.

In some embodiments, the subject is resistant or non-responsive to an ER activation inhibitor. In some embodiments, the subject is characterized by being resistant or non-responsive to an ER activation inhibitor.

In some embodiments, the ER activation inhibitor is selected from the group consisting of: an aromatase inhibitor (AI), a selective ER degrader (SERD), and a selective ER modulator (SERM). Each possibility represents a separate embodiment.

In some embodiments, the SERM is tamoxifen.

In some embodiments, the method further comprises administering to the subject a therapeutically effective amount of an ER activation inhibitor.

In some embodiments, the compound having a structure represented by Formula II and optionally the at least one additional cannabinoid are formulated within a first pharmaceutical composition and the ER activation inhibitor is formulated within a second pharmaceutical composition.

In some embodiments, the first pharmaceutical composition and the second pharmaceutical composition are administered simultaneously or sequentially, in any order.

In some embodiments, the compound having a structure represented by Formula II, optionally with the at least one additional cannabinoid, and the ER activation inhibitor are formulated in the same pharmaceutical composition.

In some embodiments, the method further comprises a step preceding the administration, wherein the step comprises selecting a subject resistant or non-responsive to an ER activation inhibitor.

In some embodiments, selecting a subject resistant or non-responsive to an ER activation inhibitor comprises determining responsiveness of a biological sample obtained or derived from the subject to at least one ER activation inhibitor, wherein low or lack of response of the biological sample to the at least one ER activation inhibitor, compared to a control, is indicative of the subject being suitable for treatment with the pharmaceutical cannabinoid composition or pharmaceutical combination disclosed herein.

In some embodiments, the pharmaceutical combination is used for sensitizing a subject afflicted with an ER-related disease to an ER activation inhibitor, wherein the subject is resistant or non-responsive to treatment with an ER activation inhibitor alone.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIGS. 7A-7H show that THC and CF2 reduce ERα protein level. (7A) Normalized intensity (treatment/control) of ERα expression levels of MCF7 cells that were treated with DMSO control, CF2, CBN, THC, or CANN14 for 18 hours. (7B) A representative western blot of ERα expression in MCF7 cells that were treated with DMSO control, CANN14, CF2, CBN, THC, or combinations thereof for 18 hours using GAPDH as the loading control. (7C) Expression levels of ESR1 gene in MCF7 cells that were incubated with DMSO control, CANN14, CF2, CBN, THC, or combinations thereof for 18 hours via real-time PCR. (7D) Expression levels of AR gene in MCF7 cells that were incubated with DMSO control, CANN14, CF2, CBN, THC, or combinations thereof for 18 hours via real-time PCR. (7E) Expression levels of CDC25A gene in MCF7 cells that were incubated with DMSO control, CANN14, CF2, CBN, THC, or combinations thereof for 18 hours via real-time PCR. (7F) Expression levels of GREB1 gene in MCF7 cells that were incubated with DMSO control, CANN14, CF2, CBN, THC, or combinations thereof for 18 hours via real-time PCR. (7G) Expression levels of PGR gene in MCF7 cells that were incubated with DMSO control, CANN14, CF2, CBN, THC, or combinations thereof for 18 hours via real-time PCR. (7H) Expression levels of TFF1 gene in MCF7 cells that were incubated with DMSO control, CANN14, CF2, CBN, THC, or combinations thereof for 18 hours via real-time PCR. Data are presented as mean±S.E.M (n=3) and statistically analyzed by one-way ANOVA (* $p<0.05$,  $p<0.005$, * $p<0.0001$).

DETAILED DESCRIPTION

In some embodiments, the present invention is directed to cannabinoid compounds, cannabinoid compositions, plant extracts comprising cannabinoids, and methods of treating or ameliorating a disease using the described cannabinoid compounds, compositions, and extracts, in a subject in need thereof. Further, the present invention, in some embodiments, is directed to a combination therapy of the cannabinoid compounds, compositions, and extracts with an ER activation inhibitor and use thereof for increasing the sensitivity of a subject characterized by resistance to the ER activation inhibitor.

Cannabinoids and Compositions

Figure 5A:
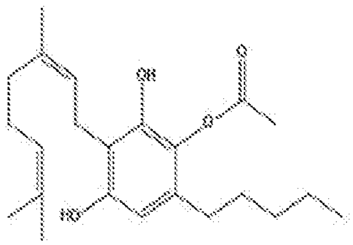
FIGS. 5A-5C show the chemical structures of (5A) the compound of the invention (also referred to herein as "CF2"); (5B) CBN, and (5C) THC.

In some embodiments, the composition comprises the compound of the invention (hereinafter "CF2", FIG. 5A) having a structure represented by Formula II:

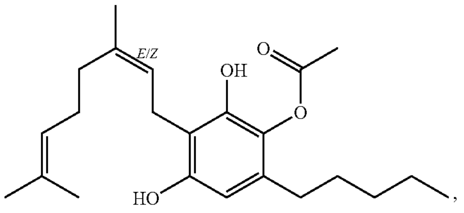

and/or any salt thereof.

In some embodiments, the compound of the invention comprises a precursor of a compound having a structure represented by Formula II. In some embodiments, a precursor comprises an acid precursor of the compound having a structure represented by Formula II. In some embodiments, the precursor is a carboxylated acid precursor of the compound having a structure represented by Formula II.

In some embodiments, the compound of the invention has a structure represented by Formula I:

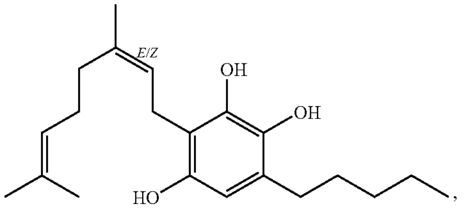

and/or any salt thereof.

It is to be understood that while the double bond in the compounds of Formulae I or II is drawn in a certain configuration, the present invention intends to encompass all structural and geometrical isomers including the E and Z isomers.

In some embodiments, the composition of the invention comprises the compound of the invention and/or any salt thereof. In some embodiments, the salt of the compound comprises any pharmaceutically acceptable salt. Such pharmaceutically acceptable salts are well-known in the art.

In some embodiments, the herein disclosed cannabinoid composition is used as an anti-ER-related disease agent.

In some embodiments, the invention relates to a composition comprising the compound of the invention as an active ingredient. In some embodiments, the invention relates to a composition comprising the compound of the invention as the active ingredient. In some embodiments, the invention relates to a composition consisting essentially of the compound of the invention. In some embodiments, the invention relates to a composition comprising CF2 as a sole active ingredient. In some embodiments, the invention relates to a composition comprising CF2 as the sole active ingredient. In some embodiments, the invention relates to a composition comprising CF2 as a sole cannabinoid. In some embodiments, the invention relates to a composition comprising CF2 as the sole cannabinoid.

In some embodiments, the composition further comprises one or more additional cannabinoids.

Figure 5B:
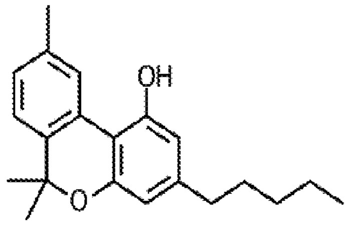
Figure 5C:
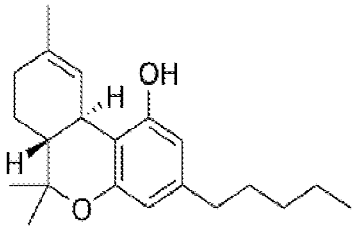

According to some embodiments, the invention relates to a composition comprising a plurality of cannabinoids. In some embodiments, the composition comprises a cannabinoid selected from: the compound of the invention, THC (e.g., $\Delta^9$-THC, FIG. 5C), CBN (cannabinol, FIG. 5B), and combinations thereof. In some embodiments, the composition comprises the compound of the invention and at least one additional cannabinoid selected from THC and CBN. In some embodiments, the composition comprises the compound of the invention and THC. In some embodiments, the composition comprises the compound of the invention and CBN. In some embodiments, the composition comprises the compound of the invention, THC, and CBN.

In some embodiments, THC is or comprises $\Delta^9$-THC. In some embodiments, THC is or comprises $\Delta^8$-THC. In some embodiments, THC is or comprises $\Delta^9$-THC and $\Delta^8$-THC. In some embodiments, THC is or comprises at least one of $\Delta^6$-THC, $\Delta^8$-THC, $\Delta^9$-THC, and $\Delta^{10}$-THC. Each possibility represents a separate embodiment.

In some embodiments, the cannabinoid is a phytocannabinoid. As used herein, a "phytocannabinoid" is a cannabinoid that originates from the *Cannabis* plant. In some embodiments, the present invention is directed to a composition derived from a plant extract. In some embodiments, a plant extract of the invention is derived from a plant comprising cannabinoids. In some embodiments, the plant extract of the invention is derived from a *Cannabis* plant. In some embodiments, the plant extract is derived from a specific species of the *Cannabis* genus. In some embodiments, the *Cannabis* species is selected from *Cannabis sativa, Cannabis indica, Cannabis ruderalis*, and a mixture or combination thereof. Each possibility represents a separate embodiment.

In some embodiments, the invention relates to a composition comprising CF2 in an amount which is more than 1% by weight of the total cannabinoid content in the composition. For example, the composition comprises CF2 in an amount which is more than 1%, 2%, 3%, 5%, 10%, 20%, 30%, 40%, 50%, 60%, 70%, 80%, 90%, 95%, 99% and up to 100% by weight of the total cannabinoid content in the composition.

In some embodiments, at least 0.1%, 0.5%, 1%, 2%, 3%, 5%, 10%, 20%, 30%, 50%, 70%, 85%, 90%, 99% and up to 100% of the cannabinoid content of the composition is the compound of the invention, or any value and range therebetween. Each possibility represents a separate embodiment of the invention. In some embodiments, the composition comprises at most 0.5%, 1%, 5%, 10%, 25%, 40%, 50%, 60%, 70%, 80%, 90%, 95%, 99% or even 100% of the compound of the invention, or any value and range therebetween. Each possibility represents a separate embodiment of the invention.

In some embodiments, at least 1%, 5%, 10%, 20%, 30%, 40%, 50%, 60%, 70%, 80%, 90%, 95%, 99% and up to 100% of the cannabinoid content of the composition is THC, or any value and range therebetween. Each possibility represents a separate embodiment of the invention. In some embodiments, the composition comprises at most 1%, 5%, 10%, 20%, 30%, 40%, 50%, 60%, 70%, 80%, 90%, 95% or 99% THC, or any value and range therebetween. Each possibility represents a separate embodiment of the invention.

In some embodiments, at least 1%, 5%, 10%, 20%, 30%, 40%, 50%, 60%, 70%, 80%, 90%, 95%, 99% and up to 100% of the cannabinoid content of the composition is CBN, or any value and range therebetween. Each possibility represents a separate embodiment of the invention. In some embodiments, the composition comprises at most 1%, 5%, 10%, 20%, 30%, 40%, 50%, 60%, 70%, 80%, 90%, 95% or 99% CBN, or any value and range therebetween. Each possibility represents a separate embodiment of the invention.

In some embodiments, the compound of the invention, and any one of THC, CBN, and any combination thereof, combined, comprise at least 45%, 50%, 60%, 70%, 80%, 85%, 90%, 97%, or 99% by weight, of the total cannabinoids of the composition, or any value and range therebetween. Each possibility represents a separate embodiment of the invention. In some embodiments, the compound of the invention, and any one of THC, CBN, and any combination thereof, combined, comprise at least 45-80%, 50-75%, 60-95%, 70-99%, 80-100%, 50-85%, 60-90%, 68-97%, or 55-99% by weight, of the total cannabinoids of the composition. Each possibility represents a separate embodiment of the invention.

In some embodiments, the compound of the invention, THC, CBN, or any combination thereof, constitutes more than 50% by weight of the cannabinoids in the composition.

In some embodiments, the composition comprises a w/w ratio of (i) the compound of the invention and (ii) THC, selected from 1:1 to 1:1,500; 1:100 to 1:1,000; 1:150 to 1:1,000; 1:200 to 1:1,000; 1:300 to 1:1,000; 1:400 to 1:1,000; 1:500 to 1:1,000; 1:600 to 1:1,000; 1:700 to 1:1,000; 1:800 to 1:1,000; 1:900 to 1:1,000; 1:500 to 1:2,000; 1:600 to 1:2,000; 1:700 to 1:2,000; 1:800 to 1:2,000; 1:900 to 1:2,000; 1:1,000 to 1:2,000; 1:1,100 to 1:2,000; 1:1,200 to 1:2,000; 1:1,300 to 1:2,000; 1:1,400 to 1:2,000; 1:1,500 to 1:2,000; 1:1,600 to 1:2,000; 1:1,700 to 1:2,000; 1:1,800 to 1:2,000; 1:1,900 to 1:2,000; 1,500:1 to 1:1; 1,400:1 to 1:1; 1,300:1 to 1:1; 1,200:1 to 1:1; 1,100:1 to 1:1; 1,000:1 to 1:1; 900:1 to 1:1; 800:1 to 1:1; 700:1 to 1:1; 600:1 to 1:1; 500:1 to 1:1; 400:1 to 1:1; 300:1 to 1:1; 200:1 to 1:1; and 100:1 to 1:1. Each possibility represents a separate embodiment of the invention.

In some embodiments, the composition comprises a w/w ratio of (i) the compound of the invention and (ii) CBN, selected from 1:1 to 1:2; 1:1 to 1:5; 1:1 to 1:7; 1:1 to 1:10; 1:1 to 1:15; 1:1 to 1:17; 1:1 to 1:20; 1:1 to 1:25; 1:1 to 1:40; 1:1 to 1:50; 1:1 to 1:100; 100:1 to 1:1; 50:1 to 1:1; 40:1 to 1:1; 25:1 to 1:1; 20:1 to 1:1; 17:1 to 1:1; 15:1 to 1:1; 10:1 to 1:1; 7:1 to 1:1; 5:1 to 1:1; and 2:1 to 1:1. Each possibility represents a separate embodiment of the invention.

In some embodiments, the composition comprises a w/w ratio of (i) CBN and (ii) THC, selected from 1:1 to 1:2; 1:1 to 1:5; 1:1 to 1:10; 1:1 to 1:15; 1:1 to 1:20; 1:1 to 1:25; 1:1 to 1:30; 1:1 to 1:40; 1:1 to 1:100; 1:1 to 1:250; 1:1 to 1:500; 1:1 to 1:750; 1:1 to 1,000; 1,000:1 to 1:1; 750:1 to 1:1; 500:1 to 1:1; 250:1 to 1:1; 100:1 to 1:1; 40:1 to 1:1; 30:1 to 1:1; 25:1 to 1:1; 20:1 to 1:1; 15:1 to 1:1; 10:1 to 1:1; 5:1 to 1:1; and 2:1 to 1:1. Each possibility represents a separate embodiment of the invention.

In some embodiments, the weight ratio of (i) the compound of the invention, (ii) CBN, and (iii) THC ranges from 1:1:1 to 1:50:2,500. In some embodiments, the weight ratio of (i) the compound of the invention, (ii) CBN, and (iii) THC ranges from 1:10:100 to 1:50:2,000. In some embodiments, the weight ratio of (i) the compound of the invention, (ii) CBN, and (iii) THC is 1:25:1,000.

According to some embodiments, the composition comprises the compound of the invention, THC, CBN, and further comprises at least one additional cannabinoid. Examples of cannabinoids include, but are not limited to, cannabidiol (CBD), cannabidivarin (CBDV), (−)-$\Delta^9$-trans-tetrahydrocannabinolic acid ($\Delta^9$-THCA), (−)-$\Delta^9$-trans-tetrahydrocannabivarin ($\Delta^9$-THCV), (−)-$\Delta^9$-trans-tetrahydrocannabivarinic acid ($\Delta^9$-THCVA), cannabivarin (CBNV), cannabicyclol (CBL), cannabigerol (CBG), cannabigerovarin (CBGV), cannabidiolic acid (CBDA), cannabichromene (CBC), cannabichromenic acid (CBCA) or any derivative thereof, and a mixture or combination thereof. Each possibility represents a separate embodiment.

In some embodiments, the least one additional cannabinoid is selected from: CBGA, CBG, CBG-C4, CBGV, CBGM, SesquiCBG, THCA, THCV (such as $\Delta^9$ THCV), THCVA (including $\Delta^9$ THCVA) CBDA, CBDA-C4, CBD-C4, CBDVA, CBDO, CBDM, CBCA, CBC, CBC-C4, CBCVA, CBCMA, CBCV, CBCO, CBNV, OH-CBN, OH-CBNA, CBEA, CBE, CBEV, CBEVA, CBDVA, CBNDA, CBND, CBL, CBT-1, CBTV-1, CBT-3, and CBT-2. Each possibility represents a separate embodiment of the invention.

As used herein, the term "plurality of cannabinoids" refers to two or more cannabinoids, e.g., at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, and at least 30, or any value and range therebetween. Each possibility represents a separate embodiment of the invention. In some embodiments, the plurality of cannabinoids of the composition are those having a relative amount of at least 2%, at least 1.5%, at least 1%, at least 0.4%, at least 0.3%, at least 0.2%, at least 0.1%, or any value and range therebetween in a *Cannabis* extract. Each possibility represents a separate embodiment of the invention.

In some embodiments, the composition consists essentially of the compound of the invention. In some embodiments, the composition consists essentially of the compound of the invention and THC, CBN, or any combination thereof.

The term "consisting essentially of" denotes that a given compound or substance constitutes the vast majority of the active ingredient's portion or fraction of the composition.

In some embodiments, consisting essentially of means that the compound of the invention constitutes at least 95%, at least 98%, at least 99%, or at least 99.9% by weight, of the active ingredient(s) of the composition, or any value and range therebetween. Each possibility represents a separate embodiment of the invention.

In some embodiments, consisting essentially of means that the compound of the invention constitutes at least 95%, at least 98%, at least 99%, or at least 99.9% by weight, of the total cannabinoids content of the composition.

In some embodiments, the composition comprises or consists of a plant extract.

As used herein, the term "extract" comprises the whole extract, a fraction thereof, a portion thereof, an isolated compound therefrom, or any combination thereof.

In some embodiments, the extract is derived from a plant material.

In some embodiments, the plant material is first dried and then extracted. In some embodiments, the plant material is air-dried. In some embodiments, the plant material is further heat treated (e.g., hot drying) and then extracted.

As used herein, treatment before extraction comprises, for example, freezing, drying, lyophilizing, or any combination thereof.

In some embodiments, the plant material is further processed prior to the extraction procedure in order to facilitate the extraction procedure. In some embodiments, processing methods prior to extraction include, but are not limited to, crushing, slicing, shredding, milling or grinding such as by using a grinder or other devices to fragment the plant parts into small pieces or powder.

In some embodiments, the cannabinoids undergo decarboxylation prior to or after the extraction procedure.

In some embodiments, the extraction comprises at least one of organic solvent extraction, carbon dioxide (dry ice) extraction, supercritical and subcritical carbon dioxide extraction, hydrocarbon extraction, rosin press, and a combination thereof. Each possibility represents a separate embodiment. In some embodiments, the extraction is a solvent-based extraction. In some embodiments, the solvent is a polar solvent. As used herein, a polar solvent includes, but is not limited to, ethanol and isopropyl. In some embodiments, the solvent is a non-polar solvent. In some embodiments, the extraction is a solvent-free extraction.

In some embodiments, the *Cannabis* derived substance used in the compositions and methods as described herein includes the compound of the invention. In one embodiment, the composition described herein comprises purified or substantially purified (e.g., greater than 80% w/w, 85% w/w, 90% w/w, 95% w/w, or 97% w/w) compound of the invention. In some embodiments of the methods described herein, purified or substantially purified (e.g., greater than 80% w/w, 85% w/w, 90% w/w, 95% w/w, or 97% w/w) compound of the invention is administered to a subject suffering from a disease or a condition as described herein.

In one embodiment, the *Cannabis* derived substances used in the compositions and methods as described herein include THC, or a functional variant thereof. In one embodiment, the composition described herein comprises purified or substantially purified (e.g., greater than 80% w/w, 85% w/w, 90% w/w, 95% w/w, or 97% w/w) THC. In some embodiments of the methods described herein, purified or substantially purified (e.g., greater than 80% w/w, 85% w/w, 90% w/w, 95% w/w, or 97% w/w) THC, or a functional variant thereof, is administered to a subject suffering from a disease or a condition as described herein.

In one embodiment, the *Cannabis* derived substances used in the compositions and methods as described herein include CBN, or a functional variant thereof. In one embodiment, the composition described herein comprises purified or substantially purified (e.g., greater than 80% w/w, 85% w/w, 90% w/w, 95% w/w, or 97% w/w) CBN. In some embodiments of the methods described herein, purified, or substantially purified (e.g., greater than 80% w/w, 85% w/w, 90% w/w, 95% w/w, or 97% w/w) CBN, or a functional variant thereof, is administered to a subject suffering from a disease or a condition as described herein.

In some embodiments, the cannabinoids disclosed herein are synthetic cannabinoids.

As used herein, the term "synthetic cannabinoids" refers to compounds that have a cannabinoid or cannabinoid-like structure and are manufactured using chemical means rather than by the plant.

In some embodiments, the cannabinoids disclosed herein are chemically synthesized cannabinoids. In some embodiments, the cannabinoids disclosed herein are biosynthetic cannabinoids.

In some embodiments, the composition is a pharmaceutical composition.

According to some embodiments, there is provided a pharmaceutical composition comprising the herein disclosed at least one cannabinoid comprising a compound having the structure of Formula (II) and a pharmaceutically acceptable carrier.

As used herein, the terms "carrier", "excipient", or "adjuvant" refer to any component of a pharmaceutical composition that is not the active agent. As used herein, the term "pharmaceutically acceptable carrier" refers to non-toxic, inert solid, semi-solid or liquid filler, diluent, encapsulating material, formulation auxiliary of any type, or simply a sterile aqueous medium, such as saline. Each possibility represents a separate embodiment. Some non-limiting examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose, hydroxypropyl cellulose, and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents and pH adjusting agents such as magnesium hydroxide, sodium hydroxide, potassium hydroxide, and aluminum hydroxide; alginic acid; pyrogen-free water; isotonic saline, Ringer's solution; ethyl alcohol and phosphate buffer solutions, as well as other non-toxic compatible substances used in pharmaceutical formulations. Each possibility represents a separate embodiment.

Some additional non-limiting examples of substances which can serve as carriers herein include stearic acid, magnesium stearate, calcium sulfate, vegetable oils, polyols, alginic acid, pyrogen-free water, isotonic saline, phosphate buffer solutions, cocoa butter (suppository base), emulsifier (e.g. carbomer, sodium lauryl sulfate), and the like. Each possibility represents a separate embodiment. Wetting agents and lubricants, as well as coloring agents, flavoring agents, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, $13^{th}$ Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, $10^{th}$ Edition (2004); and the "Inactive Ingredient Guide", U.S. Food and Drug Administration (FDA) Center for Drug Evaluation and Research (CDER) Office of Management, the contents of all of which are hereby incorporated by reference in their entirety.

Examples of pharmaceutically acceptable excipients, carriers and diluents useful in the present compositions include distilled water, physiological saline, Ringer's solution, dextrose solution, Hank's solution, and DMSO. Each possibility represents a separate embodiment. These additional inactive components, as well as effective formulations and administration procedures, are well known in the art and are described in standard textbooks, such as Goodman and Gillman's: The Pharmacological Bases of Therapeutics, $8^{th}$ Ed., Gilman et al. Eds. Pergamon Press (1990); Remington's Pharmaceutical Sciences, $18^{th}$ Ed., Mack Publishing Co., Easton, Pa. (1990); and Remington: The Science and Practice of Pharmacy, $21^{st}$ Ed., Lippincott Williams & Wilkins, Philadelphia, Pa., (2005), each of which is incorporated by reference herein in its entirety.

The presently described compositions may also be contained in artificially created structures such as liposomes, ISCOMS, slow-releasing particles, and other vehicles. Each possibility represents a separate embodiment. Liposomes include emulsions, foams, micelles, insoluble monolayers, liquid crystals, phospholipid dispersions, lamellar layers and the like. Each possibility represents a separate embodiment. Liposomes are formed from standard vesicle-forming lipids which generally include neutral and charged phospholipids and a sterol, such as cholesterol. The selection of lipids is generally determined by considerations such as liposome size and stability in the blood. A variety of methods are available for preparing liposomes as reviewed, for example, by Coligan, J. E. et al., Current Protocols in Protein Science, (1999), John Wiley & Sons, Inc., New York, and in U.S. Pat. Nos. 4,235,871; 4,501,728; 4,837,028; and 5,019,369.

The carrier may comprise, in total, from about 0.1% to about 99.99999% by weight of the pharmaceutical compositions presented herein.

A pharmaceutical composition may take any physical form necessary for proper administration. The composition comprising one or more cannabinoid compounds can be administered in any suitable form including, but not limited to, a liquid form (e.g. solutions, suspensions, or dispersions), a gel form, a semi-liquid (e.g., a liquid, such as a viscous liquid, containing some solid) form, a semi-solid (a solid containing some liquid) form, or a solid form. Each possibility represents a separate embodiment. Compositions can be provided in, for example, a tablet form, a capsule form, a liquid form, a food form, a chewable form, a non-chewable form, a transbuccal form, a sublingual form, a slow-release form, a non-slow-release form, a sustained release form, or a non-sustained-release form. Each possibility represents a separate embodiment.

A pharmaceutically-acceptable carrier suitable for the preparations of unit dosage forms of a composition as described herein for peroral administration is well-known in the art.

In some embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, sodium starch glycolate), additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), stabilizers (e.g. oils, polyethylene glycols), viscosity increasing agents (e.g. carbomer, colloidal silicon dioxide, ethyl cellulose, guar gum), lubricants (e.g. stearic acid, magnesium stearate), flow-aids (e.g. colloidal silicon dioxide), plasticizers (e.g. diethyl phthalate, triethyl citrate), polymers (e.g., poloxamers or poloxamines), and/or coatings and film forming agents (e.g. ethyl cellulose, acrylates, polymethacrylates). Each possibility represents a separate embodiment.

Methods of Use and Combination Therapy

In some embodiments, the compositions disclosed herein are suitable for and/or used in the treatment of a subject afflicted with an estrogen receptor (ER)-related disease.

According to some embodiments, there is provided a method for treating a subject afflicted with an ER-related disease, the method comprising administering to the subject a therapeutically effective amount of a compound having a structure represented by Formula II or a pharmaceutical cannabinoid composition comprising a compound having a structure represented by Formula II, thereby treating the subject afflicted with an ER-related disease.

According to some embodiments, there is provided a method for increasing or enhancing the therapeutic efficacy of an ER activation inhibitor in a subject in need thereof, the method comprising administering to a subject receiving an ER activation inhibitor a therapeutically effective amount of a compound having a structure represented by Formula II or a pharmaceutical cannabinoid composition comprising a compound having a structure represented by Formula II.

According to some embodiments, there is provided a compound having a structure represented by Formula II or a pharmaceutical cannabinoid composition comprising a compound having a structure represented by Formula II, for use in treating a subject afflicted with an ER-related disease.

According to some embodiments, there is provided a compound having a structure represented by Formula II or a pharmaceutical cannabinoid composition comprising a compound having a structure represented by Formula II for use in increasing or enhancing the therapeutic efficacy of an ER activation inhibitor in a subject in need thereof.

According to some embodiments, there is provided the use of a compound having a structure represented by Formula II for the preparation of a medicament for treating a subject afflicted with an ER-related disease.

According to some embodiments, there is provided the use of a compound having a structure represented by Formula II for the preparation of a medicament for increasing or enhancing the therapeutic efficacy of an ER activation inhibitor in a subject in need thereof.

As used herein, the term ER-related disease, refers to any disease, condition, disorder, pathology, or any combination thereof, wherein an estrogen receptor (ER), such as ER alpha, ER beta, or both, is involved in, induces, initiates, propagates, determines, or any combination or equivalent thereof, in the pathogenesis, pathophysiology, or both.

In some embodiments, an ER-related disease comprises a proliferative disease. In some embodiments, the ER-related disease comprises a cell-proliferation related disease.

As used herein, the term "proliferative disease" comprises a disease or disorder characterized by an increase of cell proliferation. In some embodiments, a subject is characterized by comprising an increased number of proliferating cells. In some embodiments, the cell proliferation is an abnormal cell proliferation. In some embodiments, the cell proliferation is an unregulated or dysregulated cell proliferation.

In some embodiments, a cell proliferation disease comprises or is cancer.

As used herein, "cancer" encompasses diseases associated with cell proliferation. Non-limiting types of cancer include, but are not limited to, carcinoma, sarcoma, lymphoma, leukemia, blastoma, and germ cells tumors. Each possibility represents a separate embodiment. In one embodiment, carcinoma refers to tumors derived from epithelial cells including, but not limited to breast cancer, prostate cancer, melanoma, lung cancer, pancreas cancer, bile duct cancer, colorectal cancer, lung cancer, non-small cell lung carcinoma (NSCLC), skin cancer (melanoma), uterine cancer, and colon cancer. Each possibility represents a separate embodiment. In one embodiment, sarcoma refers of tumors derived from mesenchymal cells including, but not limited to, sarcoma botryoides, chondrosarcoma, Ewing's sarcoma, malignant hemangioendothelioma, malignant schwannoma, osteosarcoma, and soft tissue sarcomas. Each possibility represents a separate embodiment. In one embodiment, lymphoma refers to tumors derived from hematopoietic cells that leave the bone marrow and tend to mature in the lymph nodes including, but not limited to, Hodgkin lymphoma, non-Hodgkin lymphoma, multiple myeloma, and immunoproliferative diseases. Each possibility represents a separate embodiment. In one embodiment, leukemia refers to tumors derived from hematopoietic cells that leave the bone marrow and tend to mature in the blood including, but not limited to, T-cell acute lymphoblastic leukemia, chronic lymphocytic leukemia, acute myelogenous leukemia, chronic myelogenous leukemia, hairy cell leukemia, T-cell prolymphocytic leukemia, large granular lymphocytic leukemia, and adult T-cell leukemia. Each possibility represents a separate embodiment. In one embodiment, blastoma refers to tumors derived from immature precursor cells or embryonic tissue including, but not limited to, hepatoblastoma, medulloblastoma, nephroblastoma, neuroblastoma, pancreatoblastoma, pleuropulmonary blastoma, retinoblastoma, and glioblastoma-multiforme. Each possibility represents a separate embodiment.

Non-limiting examples of ER-related diseases include breast cancer, ovarian cancer, colon cancer, endometrial cancer, endometriosis, fibrosis, dysmenorrhea, and gynecomastia. Each possibility represents a separate embodiment. In some embodiments, the ER-related disease is uterine serous carcinoma. An additional example of an ER-related disease includes precocious puberty. Without being bound by any theory or mechanism of action, it is contemplated that by reducing estrogen signaling with a compound having a structure represented by Formula II or a pharmaceutical cannabinoid composition comprising same either alone or in combination with an ER activation inhibitor, treatment or prevention of precocious puberty characterized by excess estrogen levels can be obtained.

As used herein, "increasing or enhancing the therapeutic efficacy of an ER activation inhibitor" is to be understood such that the dose of the ER activation inhibitor can be or is lower than the current practice or guidelines. In some embodiments, "increasing or enhancing the therapeutic efficacy of an ER activation inhibitor" is to be understood such that the ER activation inhibitor is provided at a low or lower dose compared to current practice or guidelines. For examples, the dose of an ER activation inhibitor may be reduced by at least 5%, 10%, 15%, 20%, 25%, 30%, 35%, 40%, 45%, 50% or more by the combination therapy of the present invention as compared to the dose of the ER activation inhibitor when administered alone.

It would be apparent to one of ordinary skill in the art, that by lowering and/or providing a low dose of an ER activation inhibitor, the amount and/or rate of adverse effects associated with the ER activation inhibitor are reduced. Thus, in some embodiments, the effect is synergistic, i.e., the therapeutic effect achieved by the combination is superior to the additive effects of the individual constituents thereby allowing the reduction in the dosage of the ER activation inhibitor as compared to mono-therapy with the ER activation inhibitor, while still achieving the same therapeutic effect with reduced incidence of side effects.

In some embodiments, treatment comprises reducing the occurrence of various risks or complications associated with ER activation inhibitors' therapy. For example, while treatment with an ER activation inhibitor may often lead to an increase in endometrial thickness, the combination therapy as disclosed herein is capable of reducing endometrial thickness to a level characteristic of normal endometrial thickness. In some embodiments, the combination therapy as disclosed herein is useful in reducing the risk of developing endometrial cancer.

In some embodiments, the subject is resistant or non-responsive to an ER activation inhibitor. In some embodiments, the subject does not respond to a standard dose of an ER activation inhibitor. Dosing of ER activation inhibitors so as to treat an ER-related disease would be apparent to one of ordinary skill in the art of medicine. In some embodiments, a subject resistant or non-responsive to ER activation inhibitor does not react to the ER activation inhibitor. In some embodiments, a subject resistant to or non-responsive to ER activation inhibitor reacts to increased ER activation inhibitor dosing. In some embodiments, increased is compared to a control. In some embodiments, a control comprises a standard ER activation inhibitor dose. In some embodiments, a subject resistant or non-responsive to ER activation inhibitor is treated with an ER activation inhibitor dosing which induces at least one adverse effect at a rate of at least 5% more as compared to a standard ER activation inhibitor dose. In some embodiments, the subject resistant or non-responsive to ER activation inhibitor shows a tumor growth inhibition of less than 50% when treated with an ER activation inhibitor alone. In some embodiments, the subject resistant or non-responsive to ER activation inhibitor shows a tumor growth inhibition of less than 30% when treated with an ER activation inhibitor alone. In some embodiments, the subject resistant or non-responsive to ER activation inhibitor shows an objective response rate of less than 30% when treated with an ER activation inhibitor alone. In some embodiments, the subject resistant or non-responsive to ER activation inhibitor shows an objective response rate of less than 20% when treated with an ER activation inhibitor alone.

As used herein, the term "ER activation inhibitor" refers to any compound capable of inhibiting ER signaling. In some embodiments, an ER activation inhibitor is an ER antagonist. In some embodiments, an ER activation inhibitor is an antibody. In some embodiments, an ER activation inhibitor is a small molecule. In some embodiments, an ER activation inhibitor is an inhibitory polynucleotide (such as RNAi, e.g., siRNA, dsRNA, or any equivalent thereof). In some embodiments, an ER activation inhibitor is a steroid analog. In some embodiments, an ER activation inhibitor is structurally similar to estrogen. In some embodiments, structurally similar denotes at least partial structural similarity such that the analog is being bound by the ER. In some embodiments, structurally similar denotes at least partial structural similarity such that the analog is being bound by the ER but fails to activate the ER. In some embodiments, structurally similar denotes at least partial structural similarity such that the analog is being bound by the ER but fails to induce translocation of the ER to the nucleus. In some embodiments, structurally similar denotes at least partial structural similarity such that the analog is being bound by the ER, but the ER fails to translocate, induce transcription of downstream genes, or a combination thereof.

Methods for determining inhibition of ER activation are common. Non-limiting examples include, but are not limited to, real-time (RT)-PCR, western blot, immunohistochemistry, immunocytochemistry, and others, some of which are exemplified and disclosed herein.

In some embodiments, an ER activation inhibitor is selected from aromatase inhibitor (AI), selective ER degrader (SERD), and a selective ER modulator (SERM). Each possibility represents a separate embodiment.

Types of ER activation inhibitors are common and would be apparent to one of ordinary skill in the art.

In some embodiments, a SERM comprises or is tamoxifen. In some embodiments, the ER activation inhibitor comprises or is toremifene and/or ospemifene. Each possibility represents a separate embodiment.

In some embodiments, the present invention provides combined therapy comprising the cannabinoid composition disclosed herein in combination with an ER activation inhibitor. In some embodiments, the combined therapy comprises combined preparations. In one embodiment, "a combined preparation" defines especially a "kit of parts" in the sense that the combination partners as defined above can be dosed independently or by use of different fixed combinations with distinguished amounts of the combination partners. When dosed independently, i.e. in separate pharmaceutical compositions, the combination partners can be administered simultaneously, concurrently, separately, or sequentially, with each possibility representing a separate embodiment. For example, the combination partners can be administered simultaneously or chronologically staggered, that is at different time points and with equal or different time intervals. The ratio of the total amounts of the combination partners, in some embodiments, can be varied in the combined preparation. In one embodiment, the combined preparation can be varied, e.g., in order to comply with the needs of a patient subpopulation to be treated or the needs of the single patient to be treated, which different needs can be due to a particular disease, severity of a disease, age, sex, or body weight as can be readily determined by a person skilled in the art.

According to some embodiments, there is provided a kit comprising: (a) at least one cannabinoid; and (b) at least one ER activation inhibitor.

According to some embodiments, there is provided a combination comprising: (a) at least one cannabinoid; and (b) at least one ER activation inhibitor.

In some embodiments, the kit or combination is for use in the treatment of ER-related disease in a subject in need thereof. In some embodiments, the at least one cannabinoid comprises a compound having a structure represented by Formula II.

In some embodiments, the at least one cannabinoid is formulated within a first pharmaceutical composition and the at least one ER activation inhibitor is formulated within a second pharmaceutical composition.

In some embodiments, the kit further comprises instructions for the formulation and/or administration of: (a) the at least one cannabinoid; and (b) the at least one ER activation inhibitor.

According to some embodiments, the at least one cannabinoid and the at least one ER activation inhibitor are administered concurrently. In some embodiments, the at least one cannabinoid and the at least one ER activation inhibitor are administered sequentially. In some embodiments, the at least one cannabinoid and the at least one ER activation inhibitor are administered subsequently.

According to some embodiments, the combination therapy as disclosed herein is useful for treating a subject afflicted with an ER-related disease. In some embodiments, the combination therapy is useful for sensitizing a subject afflicted with an ER-related disease to an ER activation inhibitor, wherein the subject is resistant or non-responsive to treatment with an ER activation inhibitor alone. The resistance or non-responsiveness to treatment with an ER activation inhibitor alone refers to primary resistance as well as secondary resistance, with each possibility representing a separate embodiment.

The term "sensitizing a subject afflicted with an ER-related disease to an ER activation inhibitor" as used herein refers to treatment of subjects who have developed resistance to the ER activation inhibitor, and/or prevention of acquired resistance to the ER activation inhibitor, and/or prevention or delay in tumor recurrence following cease of treatment with the ER activation inhibitor. Each possibility represents a separate embodiment.

In some embodiments, preparation of effective amount or dose can be estimated initially from in vitro assays. In one embodiment, a dose can be formulated in animal models, and such information can be used to determine useful doses more accurately in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosages for use in humans. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In some embodiments, the method further comprises a step preceding the administering step comprising selecting a subject who is resistant or non-responsive to an ER activation inhibitor.

In some embodiments, selecting said subject comprises determining responsiveness of a biological sample obtained or derived from the subject to at least one ER activation inhibitor.

In some embodiments, determining is performed in vitro or ex vivo. Each possibility represents a separate embodiment. In some embodiments, in vitro, ex vivo, or both, refers to the performance of the determination in a tube or a plate. In some embodiments, in vitro or ex vivo refers to a procedure that is performed outside the subject's body.

In some embodiments, a biological sample comprises any cell type obtained or derived from a subject. In some embodiments, a biological sample comprises any biological fluid derived or obtained from a subject. In some embodiments, a biological sample comprises a biopsy derived or obtained from a subject.

Methods for obtaining any type of a biological sample as described herein are common and would be apparent to one of ordinary skill in the art.

In some embodiments, a biological sample comprises a cell, fluid, biopsy, or any combination thereof, obtained or derived from a breast tissue of a subject. In some embodiments, the breast tissue comprises at least one: cancerous cell, malignant cell, a tumor, or any combination thereof.

In some embodiments, low or lack of response of the biological sample to the at least one ER activation inhibitor, compared to a control, is indicative of the subject being suitable for treatment using the pharmaceutical composition or combination of the invention. As used herein, low or lack of response as compared to a control relates to a statistically significant difference between the tested biological sample and a control. A statistically significant difference can be determined by any test known to the person skilled in the art. Common tests for statistical significance include, but are not limited to, t-test, ANOVA1 Kruskal-Wallis, Wilcoxon, Mann-Whitney and odds ratio.

In some embodiments, the method further comprises a step of administering to the subject a therapeutically effective amount of an ER activation inhibitor.

In some embodiments, the method further comprises a step of administering a therapeutically effective amount of an ER activation inhibitor to a subject administered with a therapeutically effective amount of the compound or pharmaceutical composition of the invention.

In some embodiments, the method further comprises a step of administering a therapeutically effective amount of an ER activation inhibitor to a subject determined as being suitable for treatment using the compound or pharmaceutical composition of the invention and administered with a therapeutically effective amount of the compound or pharmaceutical composition of the invention.

In some embodiments, the method further comprises a second step of determining responsiveness of a biological sample obtained or derived from a subject to at least one ER activation inhibitor, wherein the second determining step is performed after the subject has been administered with the compound or pharmaceutical composition of the invention.

According to some embodiments, the subject comprises at least one cell comprising increased ER signaling compared to control cells (e.g., cells having or characterized by a normal ER signaling).

Methods for determining ER signaling are common and would be apparent to one of ordinary skill in the art. Non-limiting examples for methods of determining ER signaling include determining the expression levels of ER downstream genes using e.g. real time PCR (RT-PCR), next generation sequencing, western blot, dot blot, enzyme linked immunosorbent assay (ELISA), and others, some of which are exemplified hereinbelow (in the Examples section).

As used herein, the terms "administering", "administration", and the like refer to any method which delivers a compound or a composition containing an active agent to a subject in such a manner so as to provide a therapeutic effect. One aspect of the present invention provides for dermal or transdermal administration of a therapeutically effective amount of a compound or composition of the invention to a subject in need thereof. Other suitable routes of administration include, but are not limited to, oral, buccal, lingual, sublingual, parenteral (e.g. subcutaneous, intravenous, or intramuscular), intratracheal, intrabronchial, intra-alveolar, topical, intraperitoneal, and intranasal. Each possibility represents a separate embodiment. In some embodiments, the administration is systemic. In some embodiments, the administration is local, namely to a specific site in a subject in need thereof. Administering the compound or composition to a specific site in the subject may be performed by any method known in the art. This may include an applicator, in the form of a gel or cream, as well as on a scaffold, wrap or bandage.

In some embodiments, the compositions for use in the methods of the present invention comprise solutions, emulsions, suspensions or dispersions which in some embodiments are aqueous and in other embodiments are non-aqueous (i.e. oil-based). The compositions typically comprise a safe and effective amount of the cannabinoid(s) of the present invention and optionally, other compounds as described herein, including excipients.

In another embodiment, the composition is administered by intravenous, intra-arterial, or intramuscular injection of a liquid preparation. In some embodiments, liquid formulations include solutions, suspensions, dispersions, emulsions, oils, and the like. In one embodiment, the composition is administered intravenously, and is thus formulated in a form suitable for intravenous administration. In another embodiment, the composition is administered intra-arterially, and is thus formulated in a form suitable for intra-arterial administration. In another embodiment, the composition is administered intramuscularly, and is thus formulated in a form suitable for intramuscular administration.

Further, in another embodiment, the composition is administered topically to body surfaces, and is thus formulated in a form suitable for topical administration. Suitable topical formulations include gels, ointments, creams, lotions, drops and the like. For topical administration, the active ingredient(s) disclosed herein, e.g., one or more cannabinoids, optionally combined with an additional appropriate therapeutic agent or agents (e.g. an ER activation inhibitor), are prepared, and applied as solutions, suspensions, or emulsions in a physiologically acceptable diluent with or without a pharmaceutical carrier.

In one embodiment, the preparation of the present invention is formulated in rectal compositions such as suppositories or retention enemas, using, e.g., conventional suppository bases such as cocoa butter or other glycerides.

In one embodiment, the preparations described herein are formulated for parenteral administration, e.g., by bolus injection or continuous infusion. In some embodiments, formulations for injection are presented in unit dosage forms, e.g., in ampoules or in multidose containers with optionally, an added preservative. In some embodiments, the composition is a suspension, a solution, or an emulsion in oily or aqueous vehicle, and contains a suspending, a stabilizing and/or a dispersing agent.

Compositions are formulated, in some embodiments, for atomization and inhalation administration. In another embodiment, compositions are contained in a container with attached atomizing means.

For inhalation or aspiration the compositions of the invention can be formulated as a solution or suspension as well as a powder. If desired, the compositions may be administered with the aid of nasal prongs, a face mask, an enclosed tent or chamber (completely or semi-sealed), an intratracheal catheter, an endotracheal tube, or a tracheostomy tube as is known in the art for achieving intratracheal, intrabronchial, or intra-alveolar administration. Each possibility represents a separate embodiment.

In some embodiments, a composition for parenteral administration includes aqueous solution of the active preparation in water-soluble form. Additionally, suspensions of the active ingredients, in some embodiments, are prepared as appropriate oily or water-based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contains suitable stabilizers or agents which increase the solubility of the active ingredient(s) to allow for the preparation of highly concentrated solutions.

In another embodiment, a composition delivered in a controlled release system is formulated for intravenous infusion, implantable osmotic pump, transdermal patch, liposomes, or other modes of administration. In one embodiment, a pump is used (Sefton, CRC Crit. Ref *Biomed. Eng.* 14:201 (1987); Buchwald et al., *Surgery* 88:507 (1980); Saudek et al., *N. Engl. J. Med.* 321:574 (1989)). In another embodiment, further polymeric materials can be used. In yet another embodiment, a controlled release system can be placed in proximity to the therapeutic target thus requiring only a fraction of the systemic dose (see, e.g., Goodson, in Medical Applications of Controlled Release, vol. 2, pp. 115-138 (1984)). Other controlled release systems are discussed in the review by Langer (*Science* 249:1527-1533 (1990)).

In one embodiment, the amount of a compound or composition to be administered will be dependent on the subject being treated, the severity of the affliction, and/or the manner of administration and are determined according to the judgment of the prescribing physician. The dosage administered will be dependent upon the age, health, and weight of the recipient, kind of concurrent treatment, if any, frequency of treatment, and the nature of the effect desired.

As used herein, the terms "treatment" or "treating" of a disease, disorder or condition encompasses alleviation of at least one symptom thereof, a reduction in the severity thereof, or inhibition of the progression thereof. Treatment does not necessarily mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life. In some embodiments, alleviated symptoms of the disease, disorder or condition include reduced cell viability, induced cell apoptosis, inhibited cell proliferation, or increased sensitivity to an ER activation inhibitor, e.g., tamoxifen.

As used herein, the term "prevention" of a disease, disorder, or condition encompasses the delay, suppression, or inhibition of the onset of a disease, disorder, or condition. As used in accordance with the presently described subject matter, the term "prevention" relates to a process of prophylaxis in which a subject is exposed to the presently described compositions prior to the induction or onset of the disease/disorder process. This could be done where an individual has a genetic pedigree indicating a predisposition toward the occurrence of the disease/disorder to be prevented. For example, this might be true for an individual whose ancestors show a predisposition toward certain types of, for example, cancer or malignancy. The term "suppression" is used to describe a condition wherein the disease/disorder process has already begun but obvious symptoms of the condition have yet to be realized. Thus, while an individual is already afflicted with the disease/disorder, no apparent signs of the disease/disorder have yet been clinically recognized. In either case, the term prophylaxis can be applied to encompass both prevention and suppression. Conversely, the term "treatment" refers to the clinical application of active agent(s) to combat an already existing condition whose clinical presentation has already been realized in a patient.

As used herein, "treating" comprises ameliorating and/or preventing.

In some embodiments, the proliferation rate of a cell contacted with the compound or composition of the invention is reduced or inhibited by at least 5%, 10%, 15%, 20%, 30%, 40%, 50%, 60%, 70%, 80%, 90% and up to 100% compared to a control cell, or any value and range therebetween. Each possibility represents a separate embodiment of the invention.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the term "about" when combined with a value refers to +10% of the reference value.

It is noted that as used herein and in the appended claims, the singular forms "a", "an", and "the" include plural referents unless the context clearly dictates otherwise. Thus, for example, reference to "a cannabinoid" includes a plurality of such cannabinoids and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a composition having at least one of A, B, and C" would include but not be limited to compositions that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein, and the laboratory procedures utilized in the present invention include molecular, biochemical, microbiological, and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), $3^{rd}$ Edition; "Current Protocols in Immunology" Volumes I-III Coligan J. E., ed. (1994); Stites et al. (eds), "Basic and Clinical Immunology" ($8^{th}$ Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Example 1

Differential Antitumor Effects of *Cannabis* Extracts on Various Breast Cancer Cell Types To demonstrate differential antitumor effects of different *Cannabis* extracts, cell death percent of three subtypes of breast cancer cell lines that were treated with 4 μg/ml of 29 different *Cannabis* extracts (CANN1-CANN29) for 24 hours was determined by PI and Hoechst staining. MIDA-MB-436 represent triple-negative tumors that do not express ER, PR, or HER; HCC1428 cells represent tumors that are ER-positive but resistant to endocrine therapy; and MCF7 cells represent tumors that are ER- and PR-positive, and sensitive to endocrine therapy. The examined extracts were divided into three groups: THC group for extracts with a high $\Delta^9$-THC concentration, THC:CBD group for extracts with equal concentrations of THC and CBD, and CBD group for extracts with a high CBD concentration.

In particular, sub-confluent MCF7, MDA-MB-436 and HCC1428 cells were seeded in 96-well plates, at $1\times10^4$ cells/well, in the appropriate growth media. Following 18-24 hours incubation, the media was replaced with phenol red free DMEM and different *Cannabis* extracts were immediately added, in triplicates, at a concentration of 4 μg/ml. The cells were incubated with the extracts for 24 hours followed by the addition of fluorescent probes (Propidium Iodide, PI—20 μg/ml, Sigma, UK; Hoechst—1.6 μM, Life Technologies Ltd, OR, USA). Cells were visualized for PI (excitation: 579/34 nm, emission: 624/40 nm) and Hoechst (excitation: 350/50 nm, emission: 455/50 nm) using IN Cell Analyzer 2000 (Cytiva, UK). Four sites were imaged in each well and the number of detected signals per well was counted and analyzed by the In Cell Investigator and Developer (Cytiva, UK). Cell Viability (%) was determined as the percentage of total viable cells (stained with Hoechst but not with PI)/total cells (stained with both Hoechst and PI)×100. The darker shades represent high percentage of dead cells and the lighter shades represent high percentage of viable cells.

Figure 1A:
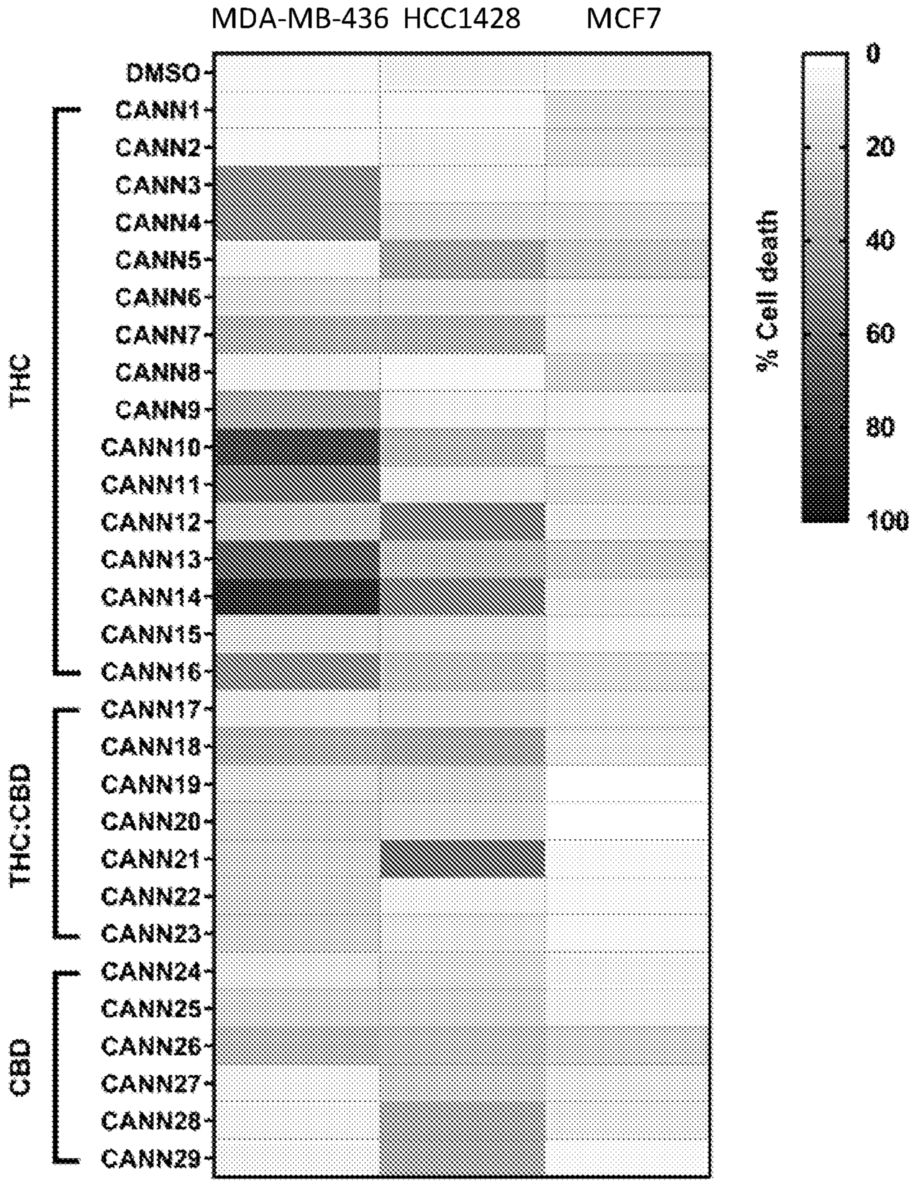
FIGS. 1A-1E show the synergetic effect of CANN14 and tamoxifen (TAM). (1A) Heat-map of cell death percent of sub-confluent MCF7, MDA-MB-436 and HCC1428 cells that were treated with 29 different *Cannabis* extracts (CANN1-CANN29) for 24 hours (DMSO represents negative control). (1B) % Cell death of MCF7 cells that were treated with *Cannabis* extracts having high THC concentrations (CANN1-CANN16; '1-16') with and without tamoxifen (TAM). (1C) % Cell death of MCF7 cells that were treated with *Cannabis* extracts having equal concentrations of THC and CBD (CANN17-CANN23; '17=23') with and without tamoxifen. (1D) % Cell death of MCF7 cells that were treated with *Cannabis* extracts having high CBD concentrations (CANN24-CANN29; '24-29') with and without tamoxifen. The results were statistically analyzed by t-test (*p<0.05, p<0.01, *p<0.001). (1E) Representative fluorescence microscopic images of PI and Hoechst staining in cells treated with DMSO control, tamoxifen only, CANN14 only and combined CANN14 and tamoxifen.

The cell lines exhibited substantial differences in their sensitivity to the *Cannabis* extracts. While MDA-MB-436 and HCC1428 cells were affected by many of the extracts, MCF7 cells were mostly resistant to *Cannabis* treatment (FIG. 1A).

Figure 1B:
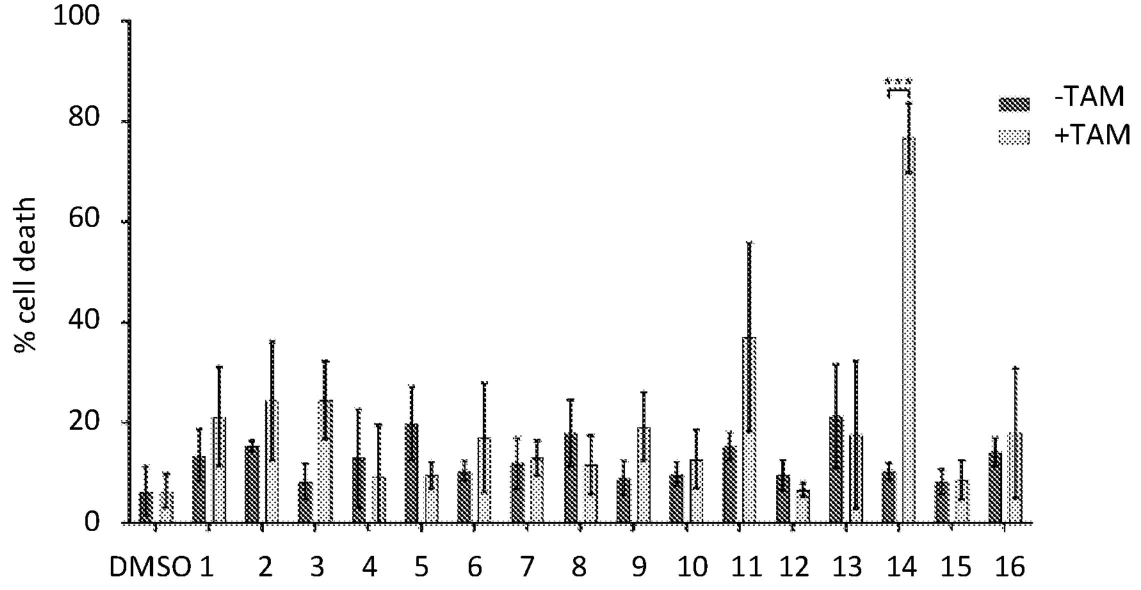
Figure 1C:
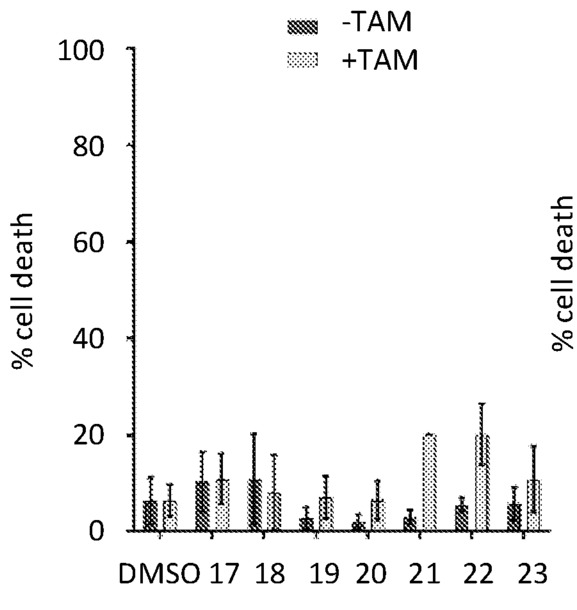
Figure 1D:
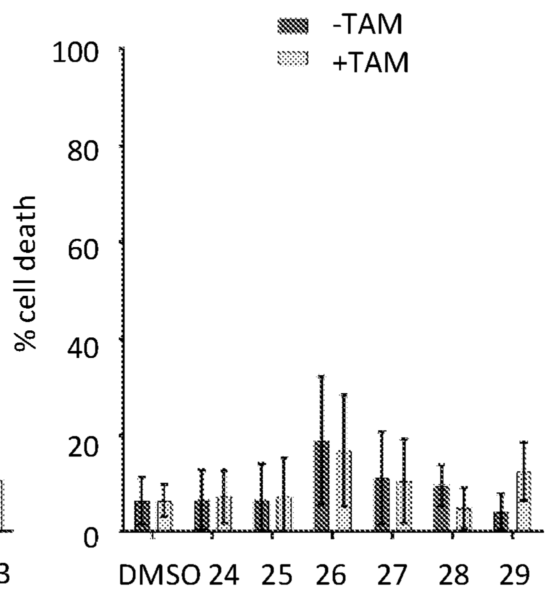
Figure 1E:
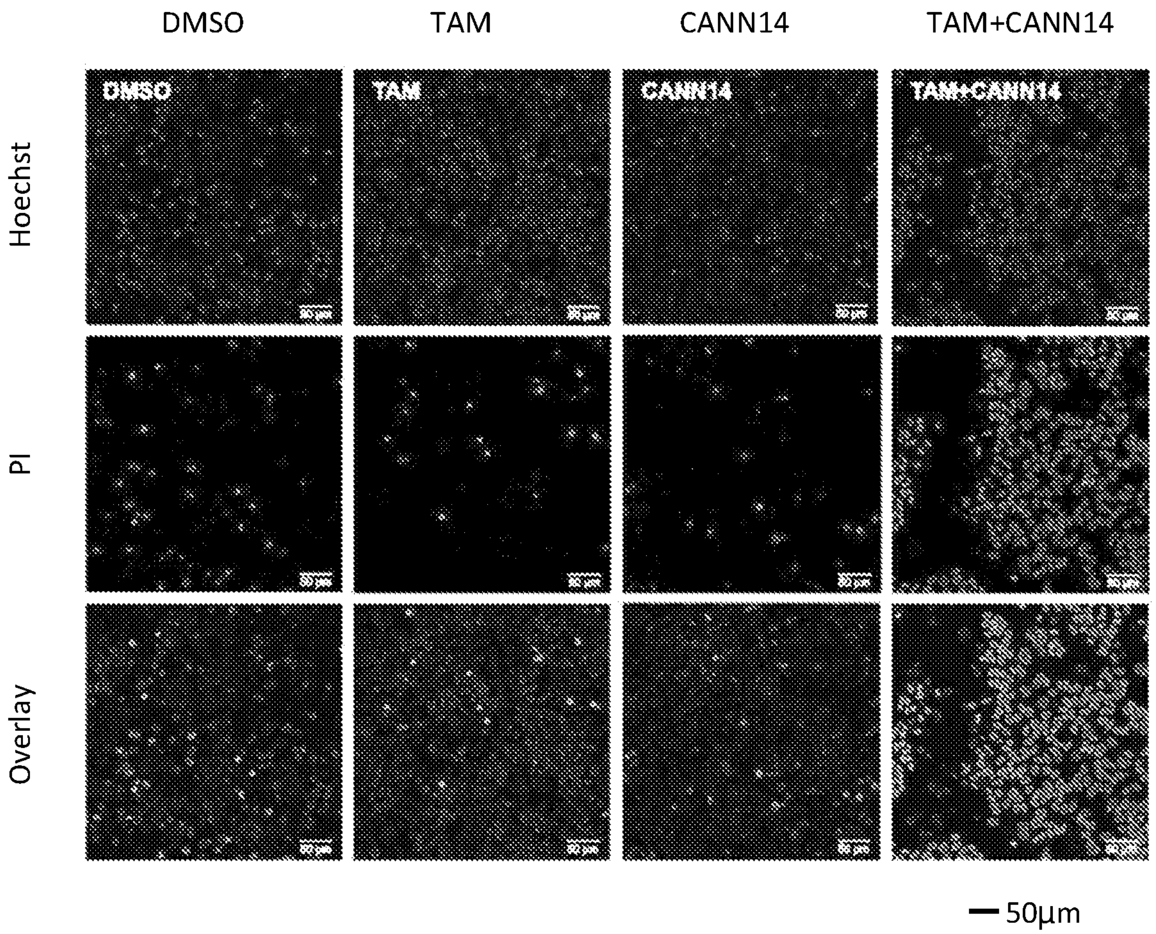

The effect of combinations of the different *Cannabis* extracts from the three groups of chemovars with tamoxifen (TAM) was then examined (FIGS. 1B-ID). While tamoxifen alone (5 μM) did not affect the viability of the cells, its combination with CANN14, a high-THC extract, showed high efficacy in inducing MCF7 cell death (FIG. 1B). This suggested that there is a synergetic effect between the unique components of this extract and the anti-breast cancer drug. FIG. 1E shows representative fluorescence microscopic images of MCF7 cells that were treated with control (DMSO), CANN14, tamoxifen (TAM), and a combination of CANN14 and tamoxifen. Elevated propidium iodide (PI) staining was observed in cells that were treated with the combination.

Figure 2A:
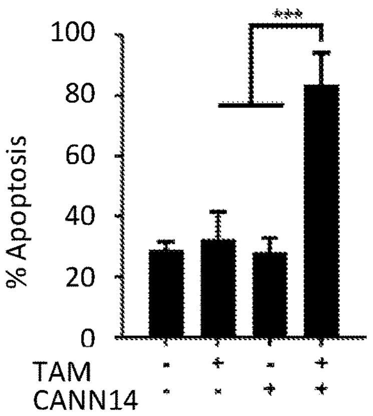
FIGS. 2A-2K show that CANN14 sensitizes breast cancer cells to tamoxifen (TAM). (2A) % Apoptosis of MCF7 cells that were treated with control, CANN14, tamoxifen, or a combination of CANN14 and tamoxifen. (2B) % Apoptosis of ZR-75-1 cells that were treated with control, CANN14, tamoxifen, or a combination of CANN14 and tamoxifen. (2C) % Apoptosis of T47D cells that were treated with control, CANN14, tamoxifen, or a combination of CANN14 and tamoxifen. (2D) Normalized intensity (treatment/control) of MCF7 cells that were incubated with control, CANN14, tamoxifen, and a combination of CANN14 and tamoxifen for 8 hours, lysed and resolved on 4-20% SDS-PAGE followed by western blotting with anti-cleaved caspase 3 and anti-GAPDH antibodies. (2E) Normalized intensity (treatment/control) of ZR-75-1 cells that were incubated with control, CANN14, tamoxifen, and a combination of CANN14 and tamoxifen for 8 hours, lysed and resolved on 4-20% SDS-PAGE followed by western blotting with anti-cleaved caspase 3 and anti-GAPDH antibodies. (2F) Normalized intensity (treatment/control) of T47D cells that were incubated with control, CANN14, tamoxifen, and a combination of CANN14 and tamoxifen for 8 hours, lysed and resolved on 4-20% SDS-PAGE followed by western blotting with anti-cleaved caspase 3 and anti-GAPDH antibodies. (2G) Representative western blots of cleaved caspase-3 in MCF7 cells that were incubated with CANN14, tamoxifen, and a combination of CANN14 and tamoxifen for 8 hours, with GAPDH as the loading control. (2H) Representative western blots of cleaved caspase-3 in ZR-75-1 cells that were incubated with CANN14, tamoxifen, and a combination of CANN14 and tamoxifen for 8 hours, with GAPDH as the loading control. (2I) Representative western blots of cleaved caspase-3 in T47D cells that were incubated with CANN14, tamoxifen, and a combination of CANN14 and tamoxifen for 8 hours, with GAPDH as the loading control. (2J) % Apoptosis (early and late) of MCF7 cell that were treated with DMSO (negative control), tamoxifen, or CANN14 for 18 hours followed by medium replacement to a new medium containing DMSO, tamoxifen or CANN14. (2K) Representative dot plots of cells treated with DMSO, CANN14, and tamoxifen for 24 hours and cells treated with tamoxifen or CANN14 for 8 hours following 18 hours treatment with CANN14 or tamoxifen, respectively. The results were statistically analyzed by one-way ANOVA (*$p<0.05$, $p<0.01$, *$p<0.001$, ****$p<0.0001$).
Figure 2B:
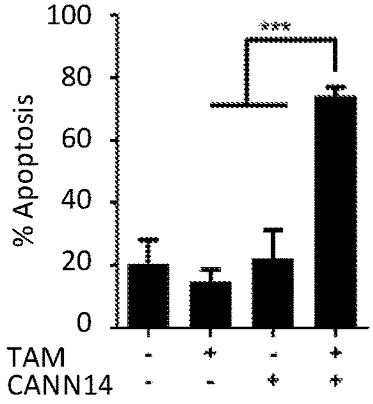
Figure 2C:
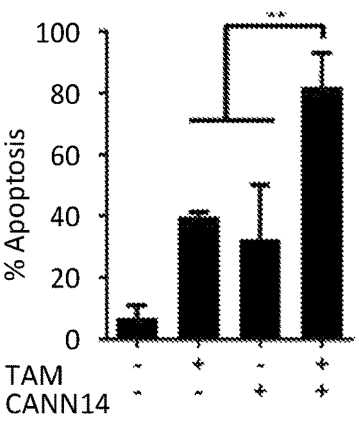

In order to examine the mechanism of cellular death, the ability of CANN14 and tamoxifen treatments, separately and together, to induce apoptosis in MCF7 cells and in two additional breast cancer cell lines of the same subtype: ZR-75-1 and T47D (all are ER-positive and sensitive to endocrine therapy) was assessed. In particular, cells were seeded in 6-well plates, at $5\times10^5$ cells per well in the appropriate growth media. Following 18-24 hours incubation, the media was replaced to phenol red-free DMEM (Biological Industries, Beit Haemek, Israel) and CANN14 extract (4 μg/ml), tamoxifen (TAM; 5 μM) or a combination of CANN14 and tamoxifen were added. Apoptosis was assessed by Annexin V/PI staining (BioLegend, CA, USA) as follows: Cells were detached from the plate using 0.25% trypsin B (Biological Industries, Beit Haemek, Israel), transferred into 15 ml test tubes and centrifuged at 250×g for 5 minutes. The supernatant was discarded, and the cell-pellets were resuspended in 200 μl of binding buffer (BioLegend, CA, USA) and transferred into flow cytometry tubes (Falcon, Mexico). 2 μl of Annexin V-APC (BioLegend, CA, USA) were added to each tube for 15 minutes and 2 μl of PI were added for 5 minutes. Apoptosis was assessed by flow cytometry using Flow cytometry Attune N×T (Life Technologies Ltd, Singapore) and analyzed by FlowJo software (Pasadena, USA). Results were calculated as percentage of positive Annexin V-FITC cells of the total events counted (50,000 events). Bar charts represent % apoptosis of at least three independent experiments, statistically analyzed by one-way ANOVA (*$p<0.05$, $p<0.01$, *$p<0.001$, ****$p<0.0001$). Cells were not affected by the treatment with CANN14 or tamoxifen alone. However, treatment with a combination of CANN14 and tamoxifen led to a significant increase in apoptosis (FIGS. 2A-2C).

Figure 2D:
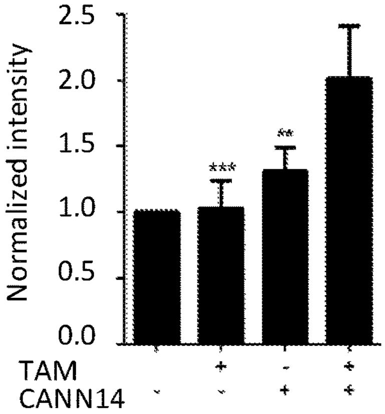
Figure 2E:
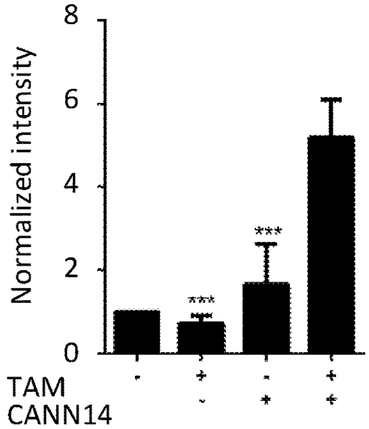
Figure 2F:
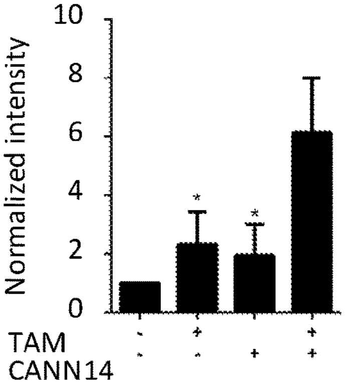
Figure 2G:
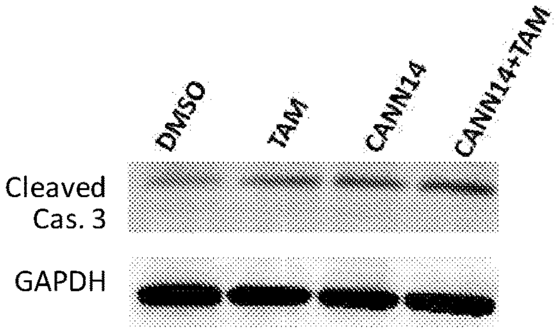
Figure 2H:
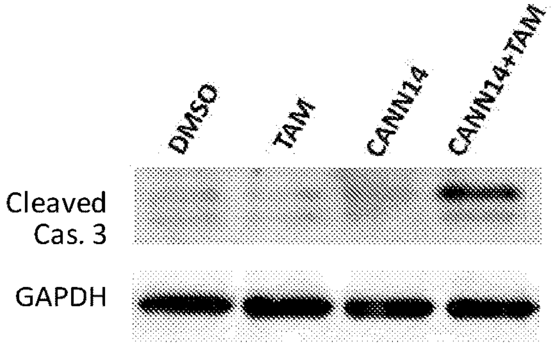
Figure 2I:
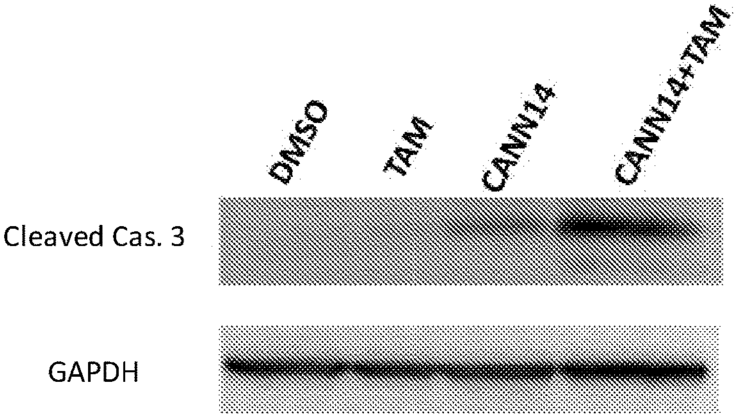

To further verify the apoptotic effect of CANN14 and tamoxifen, separately or together, the amount of cleaved caspase-3 by western blot analysis was determined (FIGS. 2D-2K). In particular, MCF7, ZR-75-1, and T47D cells were incubated with 4 μg/ml CANN14, 5 μM tamoxifen, and a combination of CANN14 and tamoxifen for 8 hours with GAPDH as the loading control. Cells were lysed and resolved on 4-20% SDS-polyacrylamide gel electrophoresis (PAGE) (Life Technologies, Burlington, Canada) and electrophoretically transferred to a nitrocellulose membrane. Membranes were blocked with TBS-T buffer containing 5% Bovine Serum Albumin (BSA) for 1-2 hours at room temperature or overnight at 4° C. The blots were then incubated with cleaved caspase-3 CST-9664S antibody overnight at 4° C., followed by incubation with HorseRadish Peroxidase (HRP) labeled matching secondary antibodies (Abcam, UK). Immunoreactive bands were detected by Enhanced Chemiluminescence (Millipore, MA, USA) and visualized using ImageQuant™ LAS 4000. Intensities were quantified using ImageJ software as treatment/control (FIGS. 2D-2F). Each data point represents mean normalized intensity of at least three independent experiments. Statistical analysis was performed by one-way ANOVA (*$p<0.05$, $p<0.01$, *$p<0.001$, ****$p<0.0001$). Either CANN14, tamoxifen or both resulted in increased induction of cleaved caspase-3, with statistically significant increase for cells treated with a combination of CANN14 and tamoxifen relative to cells treated with DMSO control. Representative blots of cleaved caspase-3 in MCF7, ZR-75-1, and T47D cells are shown in FIGS. 2G, 2H, and 2I, respectively.

Figure 2J:
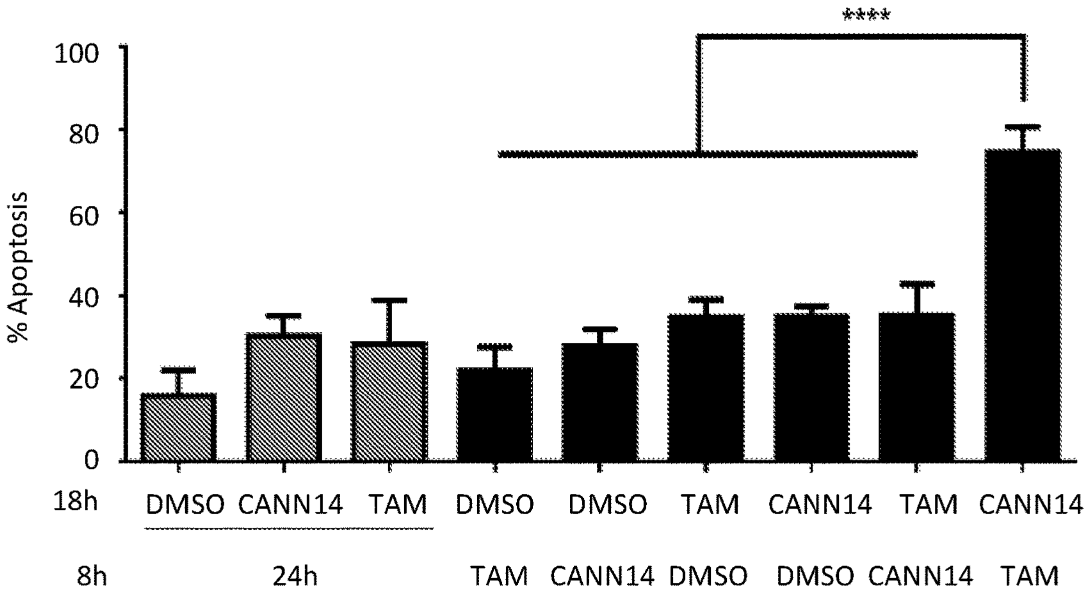
Figure 2K:
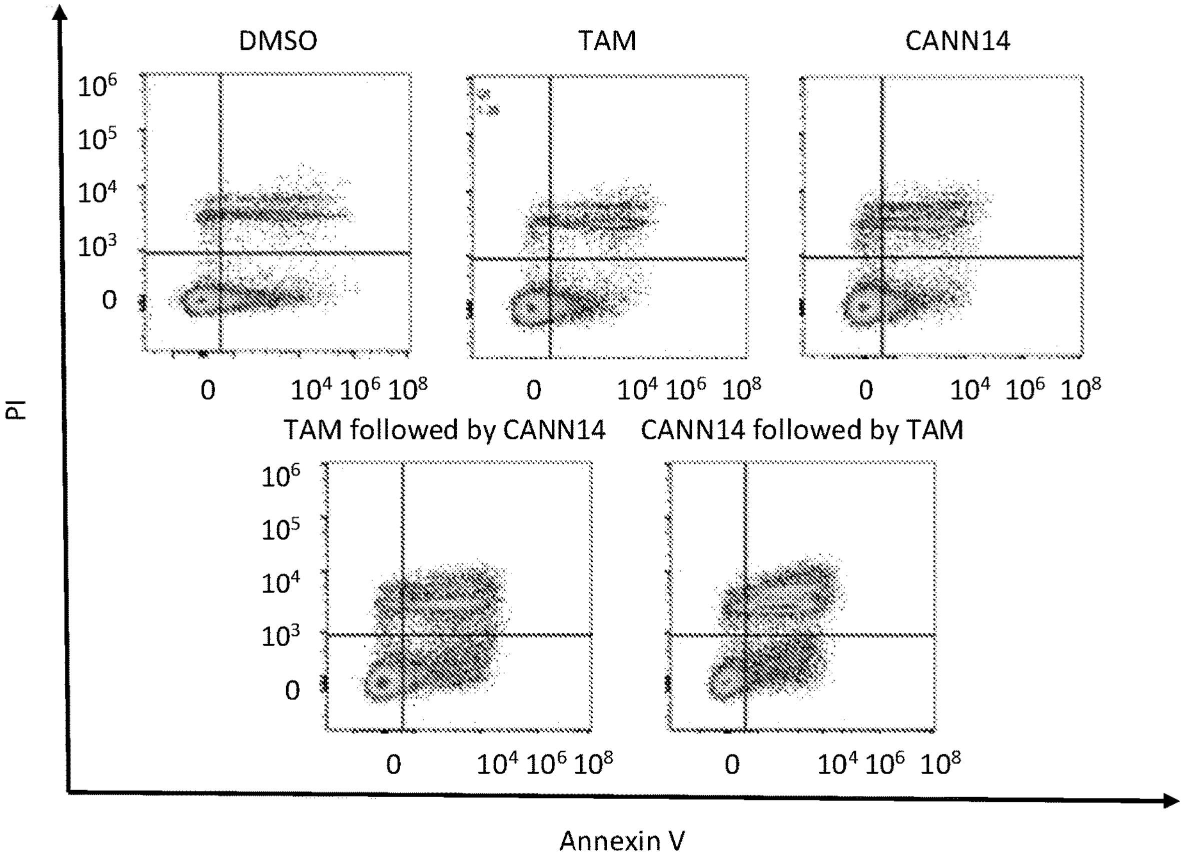

To further substantiate the synergistic effect between CANN14 and tamoxifen, the MCF7 cells were exposed to each substance sequentially and the apoptotic effect was examined by flow cytometry. In particular, cells were treated with DMSO (negative control), 5 μM tamoxifen (TAM) or 4 μg/ml CANN14 for 18 hours. Then, the medium was replaced with a new medium containing DMSO, 5 μM tamoxifen or 4 μg/ml CANN14. Apoptosis (early and late) was assessed by Annexin V/PI staining using flow cytometry. Results were calculated as percent of apoptotic cells from total counted cells. The only treatment that resulted in an increase in the percent of cell death, relative to the non-sequential treatments of either DMSO, CANN14 or tamoxifen, was the addition of tamoxifen to cells that were pretreated with CANN14 (FIG. 2J). FIG. 2K shows representative dot plots of cells that were treated with DMSO, CANN14 (4 μg/ml) and tamoxifen (TAM, 5 μM) as single agents (upper panel), and cells that were first treated with tamoxifen or CANN14 for 8 hours followed by 18 hours treatment with tamoxifen (5 μM) or CANN14 (4 μg/ml) and vice versa (lower panel). The double stained population of cells was significantly larger for cells treated first with CANN14 and then with tamoxifen.

Figure 3A:
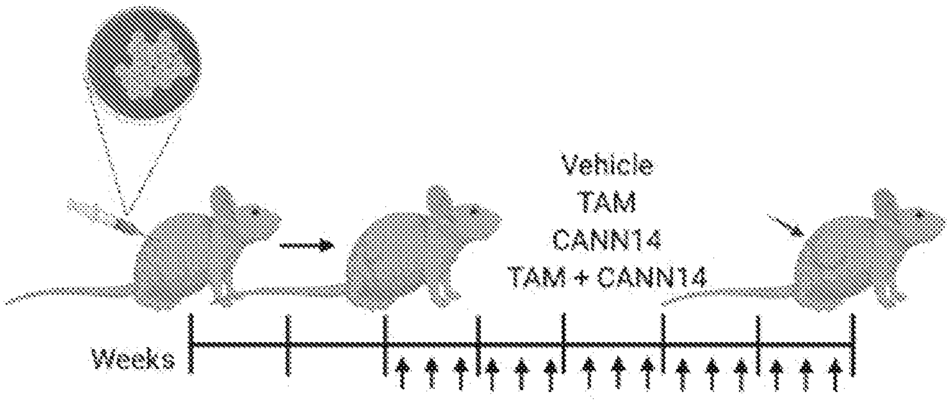
FIGS. 3A-3B show an in-vivo study using MCF7 cells demonstrating a synergetic effect of CANN14 and tamoxifen. (3A) Illustration of the in-vivo model used in the study. (3B) Growth curve of ectopic tumor volume. (●) control; (□) tamoxifen (TAM); (Δ) CANN14; and (▼) CANN14+ tamoxifen (TAM).
Figure 3B:
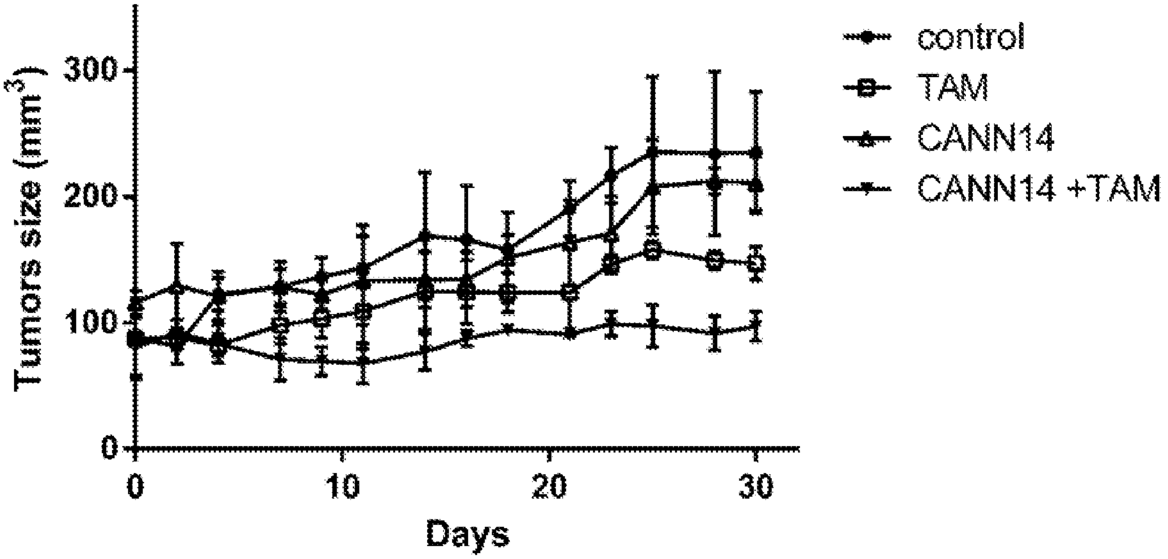

The proapoptotic effect of CANN14 in combination with tamoxifen was then tested in-vivo in a mouse model. In particular, immunodeficient six weeks-old female nude mice (Envigo, Jerusalem, Israel) were injected with $6\times10^6$ MCF7 cells subcutaneously to the right flank. The tumors were allowed to develop for two weeks until reaching a volume of 100 $mm^3$ as determined using an external caliper. The animals were then randomly assigned to the different experimental groups and treatments were conducted for additional five weeks (FIG. 3A). Treatment included three times weekly intraperitoneal (IP) injections of CANN14 at a dose of 25 mg/kg and tamoxifen at a dose of 2 mg/kg or a combination of CANN14 and tamoxifen. Control animals received the corresponding vehicles with the same pattern and route of administration. The volumes of the tumors were calculated according to the formula (length×width$^2$)/2. Animals were sacrificed after one month of treatment and the tumors' weights were measured. Treated mice showed a trend of smaller tumor sizes, and this trend was most profound for mice treated with a combination of CANN14 and tamoxifen (FIG. 3B).

Example 2

Composition of Phytocannabinoids Responsible for the Antitumor Effects

Figure 4A:
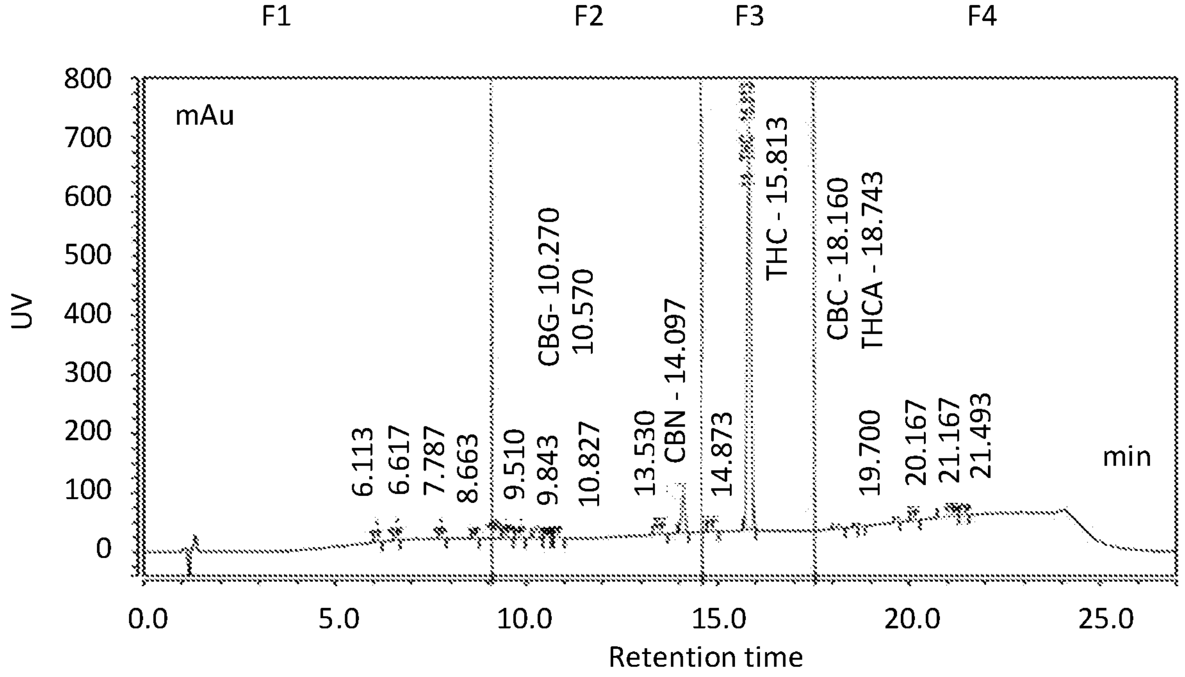
FIGS. 4A-4G show fractionation of CANN14 and the effects of CANN14 fractions in combination with tamoxifen (TAM). (4A) HPLC spectrum of CANN14 fractionized to F1-F4 according to hydrophobic gradient. (4B) % Apoptosis of MCF7 cells treated with F1-F4, THC, CANN14, and tamoxifen. (4C) % Apoptosis of MCF7 cells treated with F2A-F2D, THC, CANN14, and tamoxifen. (4D) % Apoptosis of MCF7 cells treated with CF2, CBN, THC, CANN14, and tamoxifen. (4E) % Apoptosis of T47D cells treated with CF2, CBN, THC, CANN14, and tamoxifen. (4F) % Apoptosis of ZR-75-1 cells treated with CF2, CBN, THC, CANN14, and tamoxifen. (4G) % Apoptosis of MCF7 cells treated with THC, CBN and CF2 at different ratios as present in the CANN14 extract in combination with tamoxifen. Bars represent % apoptosis of at least three independent experiments. Data are presented as mean±S.E.M (n=3) and statistically analyzed by one-way ANOVA (* $p<0.05$,  $p<0.005$, * $p<0.0001$ relative to DMSO control, $ relative to CF2).
Figure 4B:
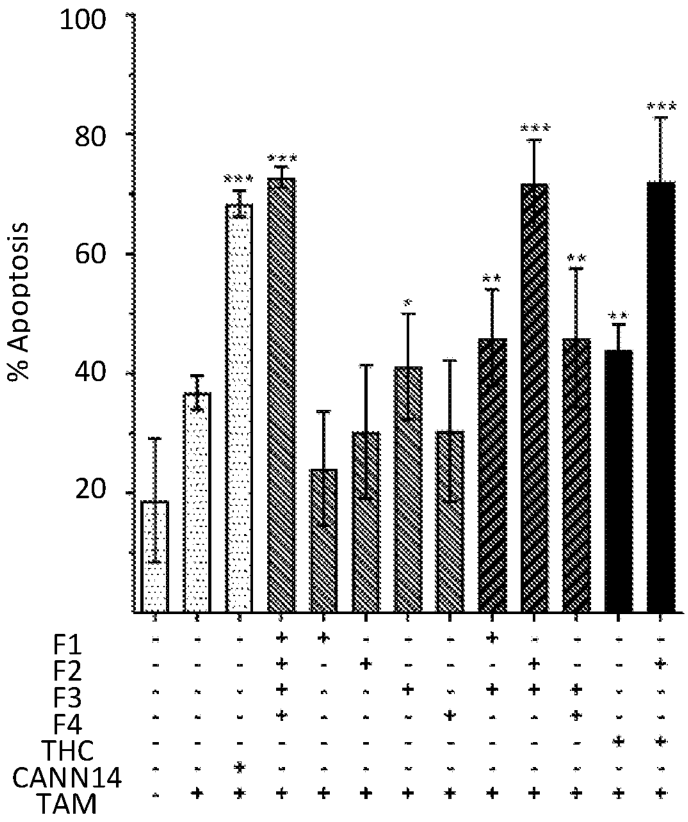

To reveal the specific substances responsible for the synergetic effect of tamoxifen and CANN14, CANN14 extract was fractionized using a semi-prep HPLC according to a hydrophobic gradient and four fractions (F1-F4) were obtained (FIG. 4A). Each fraction was normalized according to the main phytocannabinoids in the fraction. MCF7 cells were exposed to each fraction individually or to different combinations of fractions for 18 hours followed by the addition of tamoxifen for 8 hours. Apoptosis was measured by flow cytometry. As shown in FIG. 4B, exposure to each fraction separately with tamoxifen did not affect the cells. However, the combination of F3 and F2 with tamoxifen led to the highest apoptotic rate, similar to the whole CANN14 extract and tamoxifen. As F3 is dominated by $\Delta^9$-THC, a combination of pure $\Delta^9$-THC (95%) with F2 with or without TAM was tested. The combination of $\Delta^9$-THC (95%), F2, and tamoxifen was found to lead to the same apoptosis rate as the combination of F3, F2, and tamoxifen.

Figure 4C:
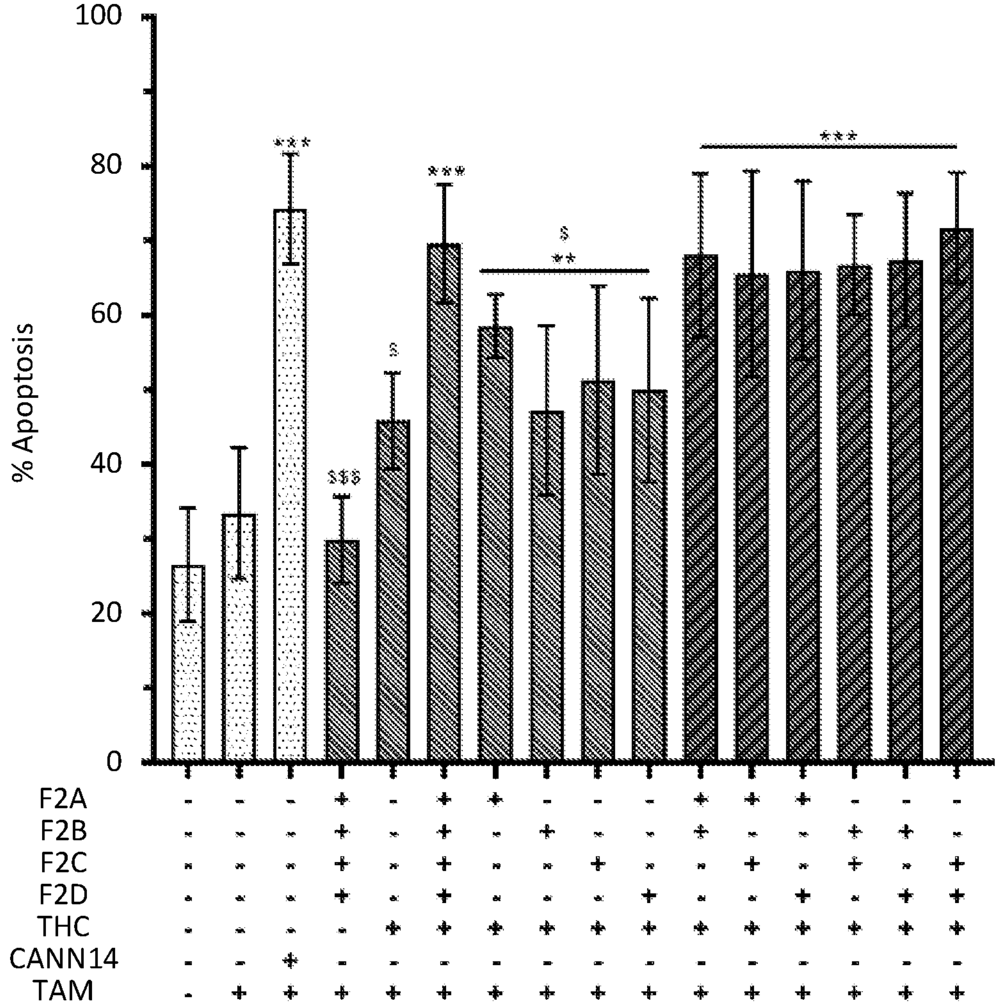
Figure 4D:
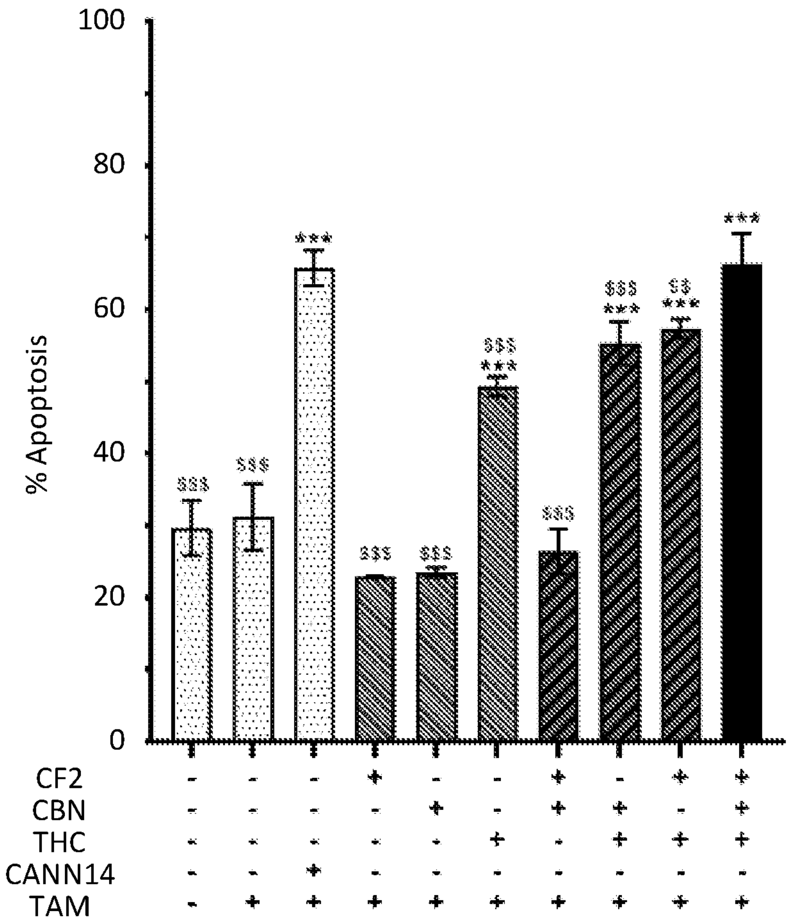
Figure 4E:
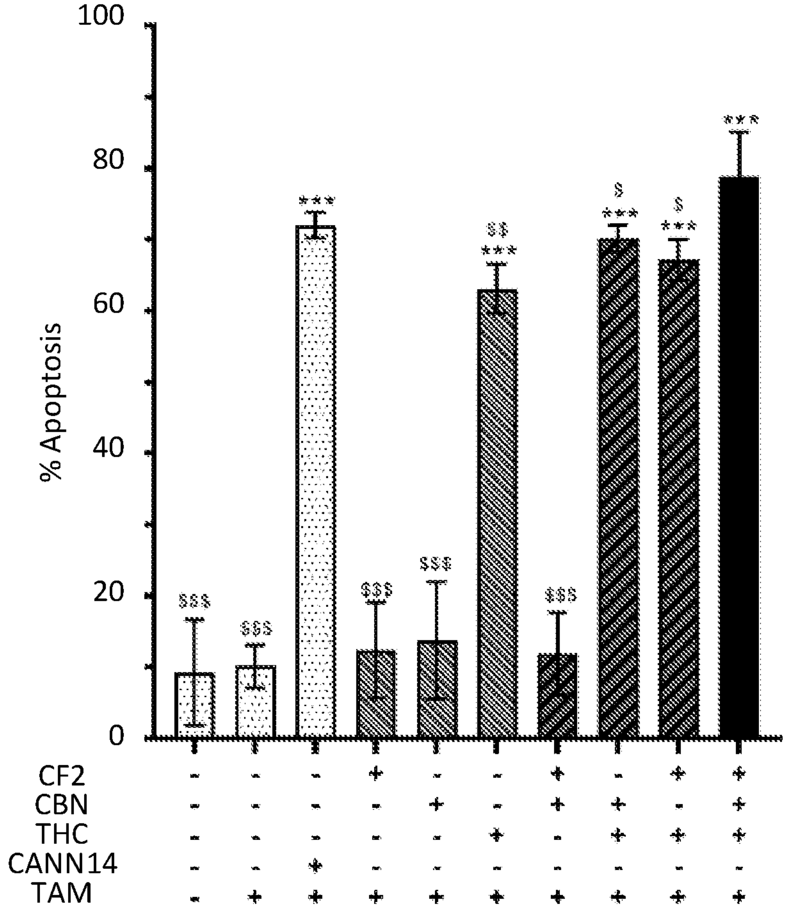
Figure 4F:
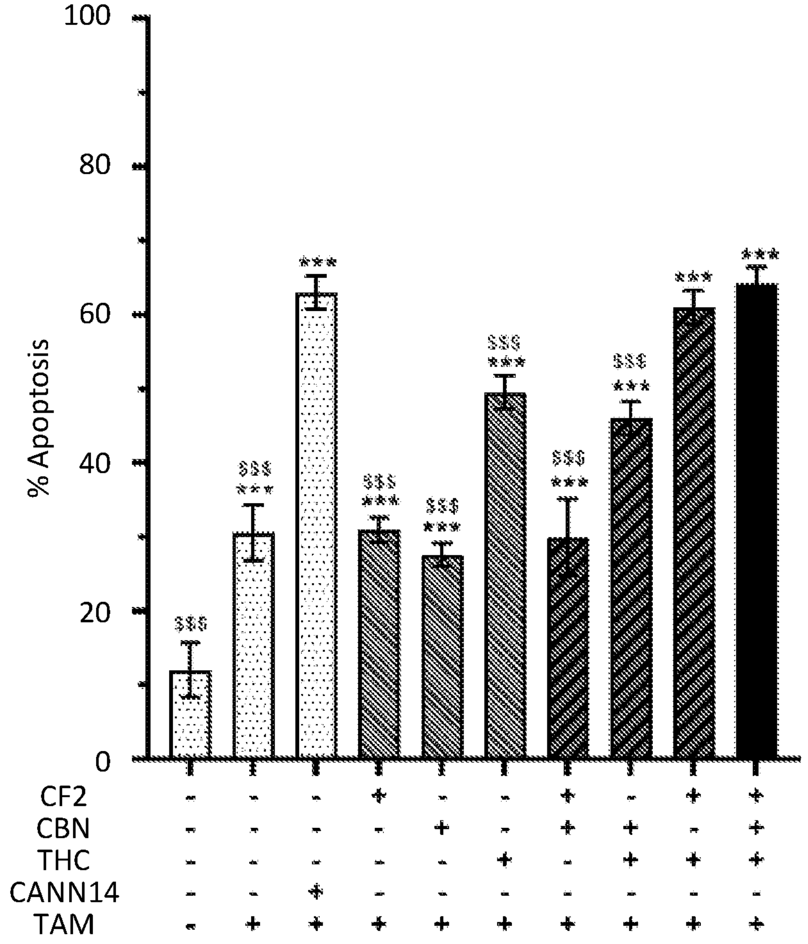
Figure 4G:
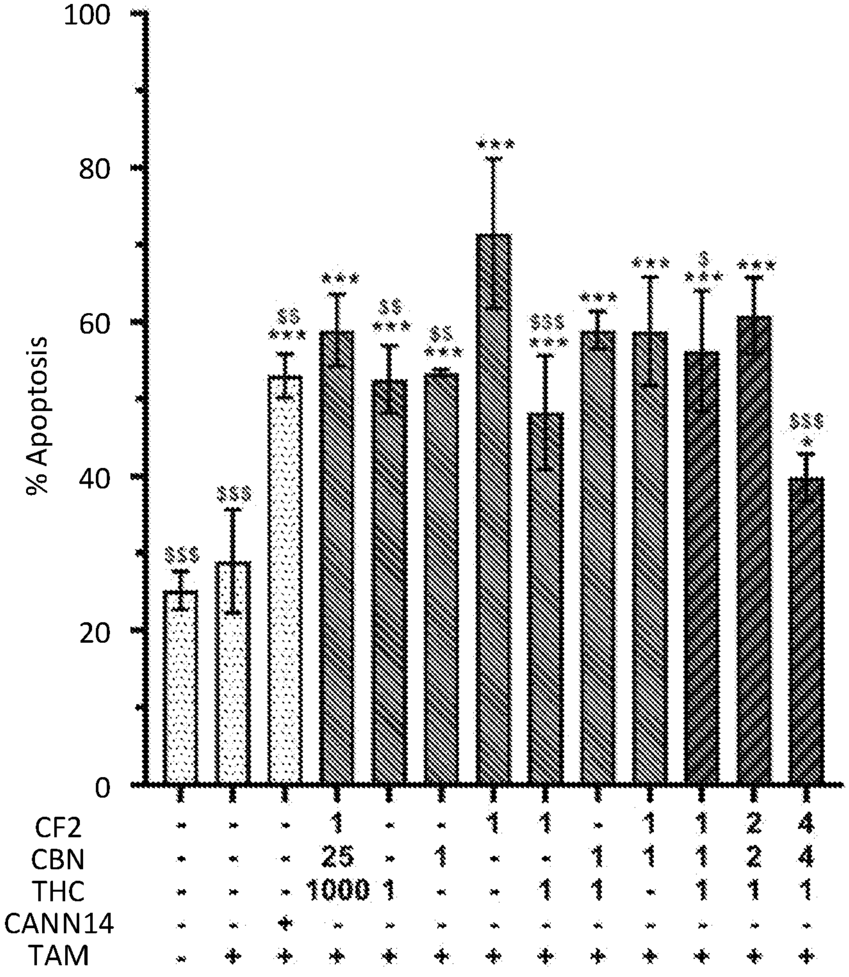

F2 was then refractured to four different subfractions (F2A-F2D) which were tested for their effect on MCF7 cells, either individually or in different combinations, with or without pure THC (FIG. 4C). Each subfraction separately with tamoxifen had no significant effect. However, all possible combinations with pure THC led to the same apoptotic rate as CANN14 and tamoxifen. LS-MS analysis of subfractions F2A-F2D revealed that the phytocannabinoids cannabinol (CBN) and the previously unidentified CF2 were found in three of the four subfractions. MCF7, T47D, and ZR-75-1 cells were then treated with either pure THC, CBN or enriched fraction of CF2 (70%), separately or in combination followed by the addition of tamoxifen (FIGS. 4D, 4E, and 4F, respectively). Combinations with THC increased the apoptotic rate, and it was significantly increased when all three cannabinoids were combined, similar to the effect of the whole extract. Since THC is much more abundant in CANN14 than CBN (40:1, respectively) or CF2 (1,000:1, respectively), different ratios of THC, CBN and CF2 were tested in combination with tamoxifen using MCF7 cells (FIG. 4G). In particular, a ratio of 1:25:1,000 of CF2, CBN, and THC as present in the CANN14 extract as well as ratios of 1:1:1, 2:2:1, and 4:4:1 were used. At higher concentrations, CF2 alone was able to induce the same apoptotic effect as the original combination of the three phytocannabinoids. The effect was even significantly superior to the CANN14 whole extract.

Further purification of CF2 was performed using a semi-prep HPLC based on an analytical method by UHPLC and elucidation of the structure was performed by $^{1}H$ NMR (400 MHz, $CDCl_3$). CF2 was then synthesized and characterized by $^{1}H$ NMR. The chemical shifts of the purified and synthetic CF2 were substantially identical: $^{1}H$ NMR (400 MHz, $CDCl_3$) δ 6.26 (1H, Ar), 5.32 (1H, OH), 5.26 (1H CH, t), 5.15 (1H, OH), 5.04 (1H, CH, t), 3.4 (2H, $CH_2$, d), 2.37 (2H, $CH_2$, d), 2.34 (3H, Ac, s), 2.05-2.09 (4H, $CH_2$—$CH_2$, m), 1.79 (3H, $CH_3$, s), 1.67 (3H, $CH_3$, s), 1.59 (3H, $CH_3$, s), 1.52 (2H, $CH_2$, m), 1.29-1.31 (4H, $CH_2$—$CH_2$, m), 0.88 (3H, $CH_3$, t).

Example 3

Effects of Specific *Cannabis* Extracts and Components

Figure 6A:
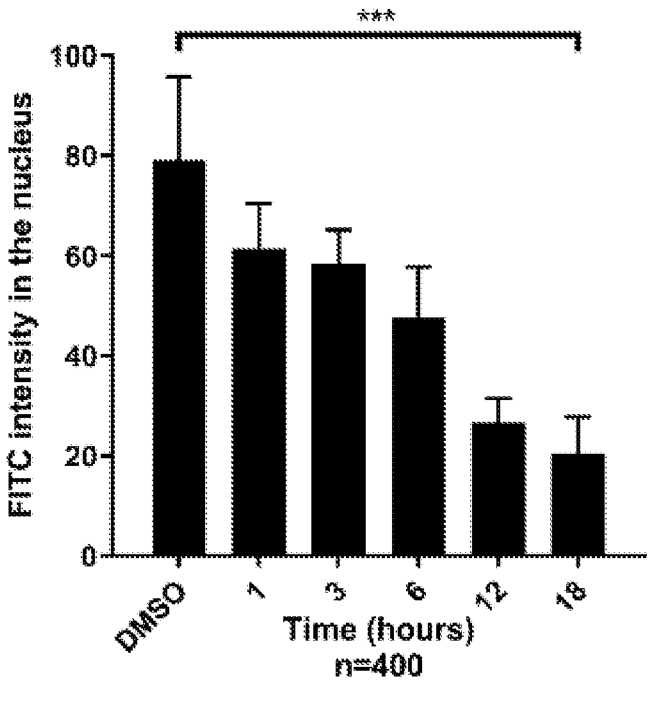
FIGS. 6A-6M show that CANN14 reduced ERα's protein level, expression level and activity. (6A) FITC intensity in the nucleus of MCF7 cells that were incubated with CANN14 for the indicated number of hours. (6B) Representative images of nuclei stained with DAPI, and ERα stained with FITC fluorescent antibody of cells treated with DMSO (upper panel) and CANN14 (lower panel) for 18 hours. (6C) Quantification of ERα protein level in MCF7 cells that were incubated with CANN14 or DMSO for 18 hours, via western blot analyses with GAPDH as the loading control. (6D) A representative western blot of MCF7 cells that were incubated with CANN14 or DMSO for 18 hours with GAPDH as the loading control. (6E) Quantification of ERα protein level in MCF7 cells that were incubated with CANN14 or DMSO for 18 hours followed by nuclear (Nuc) and cytoplasmic (Cyt) fractions extraction and western blot analysis with GAPDH as the cytoplasmic fraction marker and histone H3 as the nuclear fraction marker. (6F) A representative western blot of cells that were incubated with CANN14 or DMSO for 18 hours followed by nuclear (Nuc) and cytoplasmic (Cyt) fractions extraction. (6G) Relative estrogen receptor 1 (ESR1) expression level in MCF7 cells that were incubated with CANN14 or DMSO for 18 hours and as measured by real-time PCR analysis. (6H) ERE-luciferase activity of MCF7 cells that were treated with CANN14 for the indicated hours. (6I) Expression levels of AR gene in MCF7 cells that were incubated with CANN14 or DMSO for 18 hours via real-time PCR. (6J) Expression levels of CDC25A gene in MCF7 cells that were incubated with CANN14 or DMSO for 18 hours via real-time PCR. (6K) Expression levels of GREB1 gene in MCF7 cells that were incubated with CANN14 or DMSO for 18 hours via real-time PCR. (6L) Expression levels of PGR gene in MCF7 cells that were incubated with CANN14 or DMSO for 18 hours via real-time PCR. (6M) Expression levels of TFF1 gene in MCF7 cells that were incubated with CANN14 or DMSO for 18 hours via real-time PCR. Data are presented as mean±S.E.M (n=3) and statistically analyzed by one-way ANOVA (* $p<0.05$,  $p<0.005$, * $p<0.0001$).
Figure 6B:
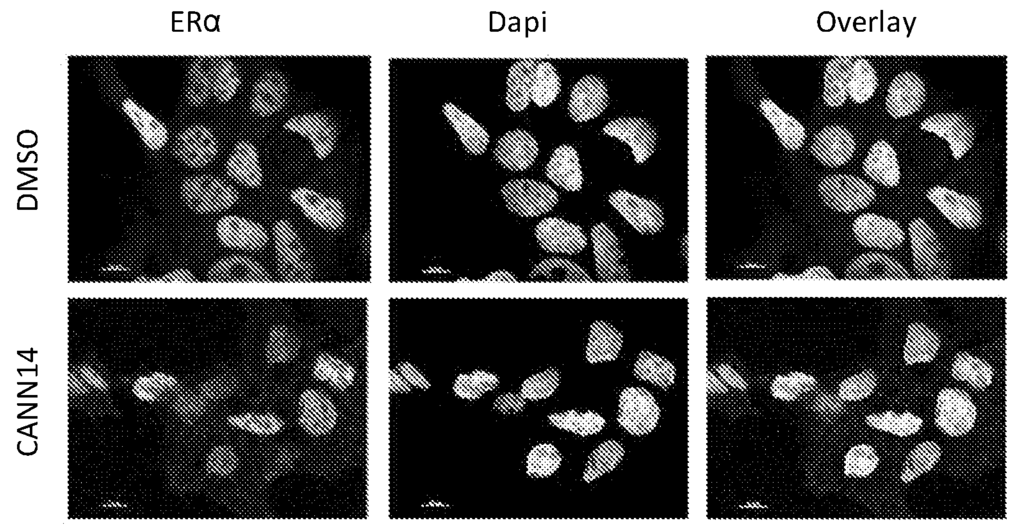
Figure 6C:
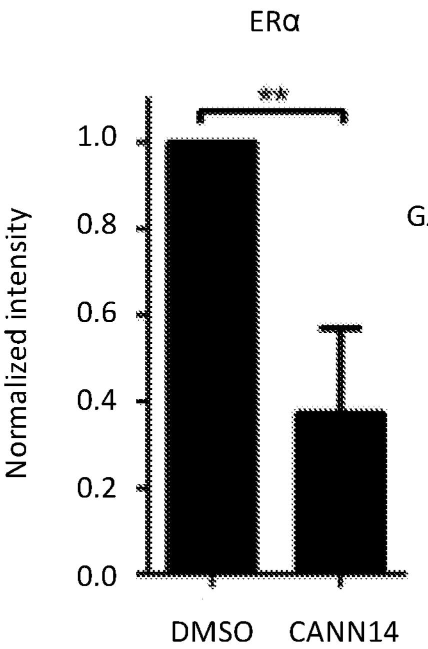
Figure 6D:
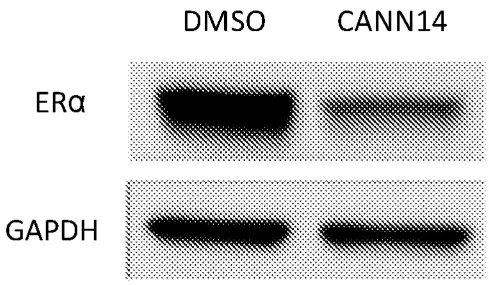
Figure 6E:
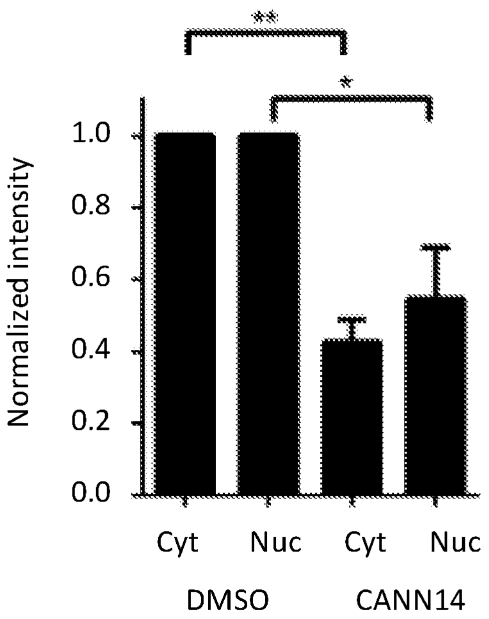
Figure 6F:
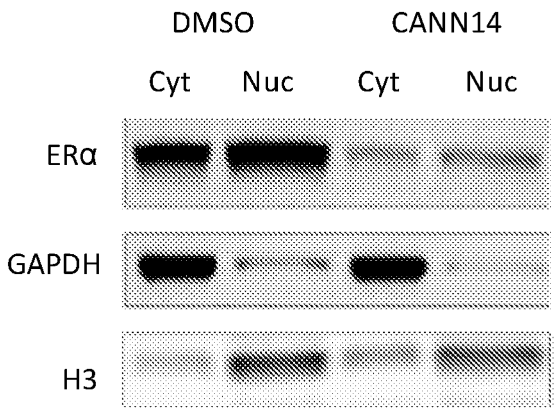

As tamoxifen is a SERM that acts as an ERα antagonist which prevents its translocation to the nucleus, the effect of CANN14 on ERα translocation using confocal imaging analysis was examined. In particular, cells were seeded in poly-D-Lysine (PDL, 1:100) on pre-coated 13 mm slides (Bar-Naor, Israel) at $1\times10^5$ cells per slide in the appropriate growth medium. Following 18-24 hours incubation, the medium was replaced to phenol red-free DMEM (Biological Industries, Beit Haemek, Israel) and *Cannabis* extracts were added (4 μg/ml) for the indicated number of hours. The cells were fixed with 4% paraformaldehyde (PFA) for 15 minutes at room temperature. Then, the cells were blocked and permeabalized with a blocking buffer containing 0.5% triton and 5% goat serum (Sigma, UK) for 1 hour at room temperature. For florescence visualization, cells were incubated with a cocktail of ERα antibody (CST, MA, USA) (1:100) in 1% goat serum-PBS overnight at 4° C. The slides were then washed three times with T-BST containing 0.25% Tween (Sigma, UK) and incubated with a secondary antibody cocktail of goat anti-rabbit AlexaFluor 488 (Abcam, UK) diluted 1:500 in blocking buffer. The nuclear staining was accomplished with florescent mounting medium with Dapi (GBI Labs, WA, USA). Cells were visualized for Dapi (excitation: 365 nm, emission: 455/50 nm) and AlexaFluor 488 (excitation: 470/40 nm, emission: 525/50 nm) using LSM 710 laser scanning confocal microscope. ERα immunostained slides were quantified by Image Visualization and Analysis Software. ERα intensity was measured only in the nucleus (marked with DAPI). The intensity of ERα in the nucleus of MCF7 cells was reduced with time, and the reduction was significant at 18 hours after treatment with CANN14 relative to DMSO control (FIGS. 6A-6B). Next, the protein levels of ERα after 18 hours of CANN14 treatment were examined. ERα protein level was significantly reduced in the whole lysates (FIGS. 6C-6D), the reduction was seen in the cytoplasm and in the nucleus (FIGS. 6E-6F).

Figure 6G:
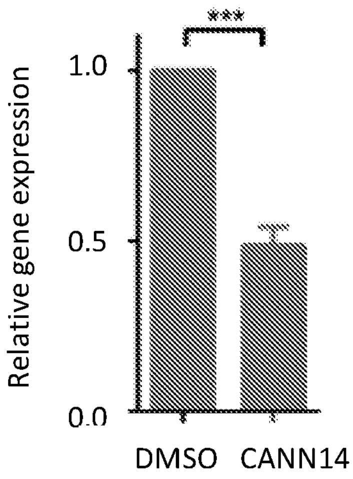
Figure 6H:
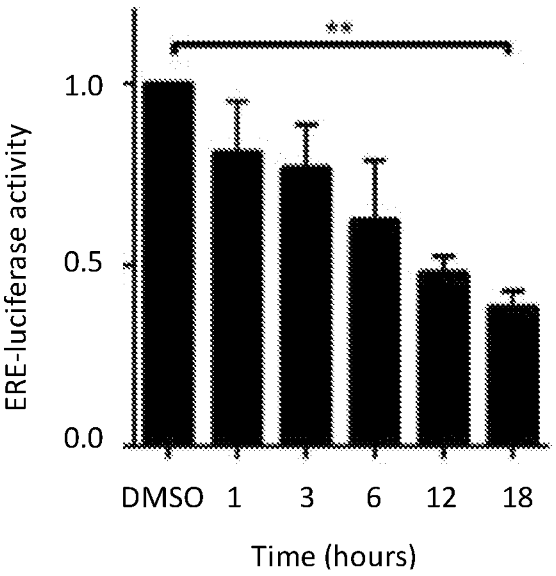
Figure 6I:
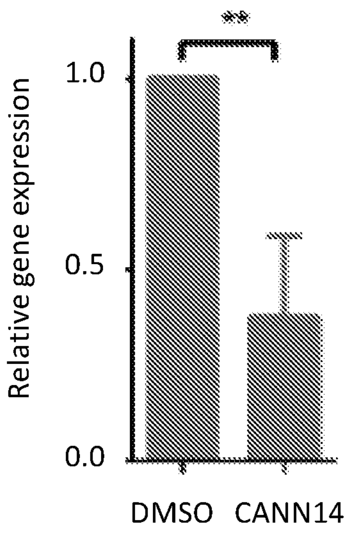
Figure 6J:
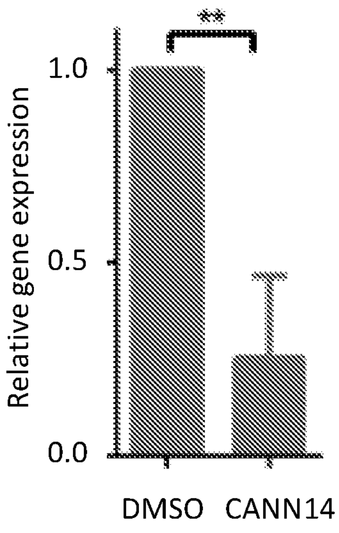
Figure 6K:
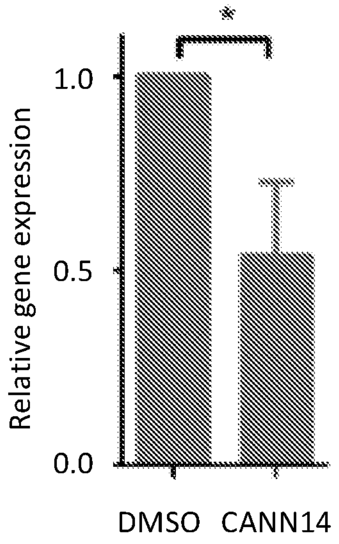
Figure 6L:
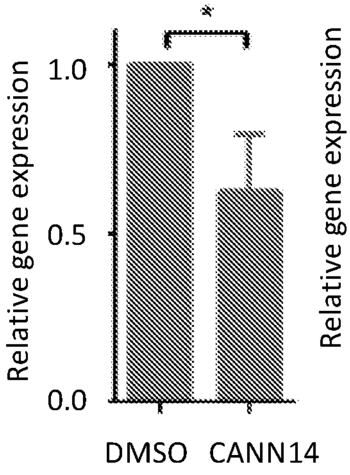
Figure 6M:
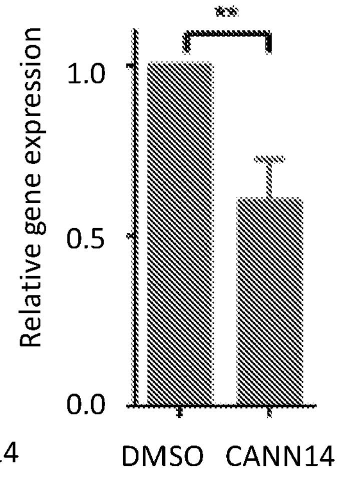
Figure 7A:
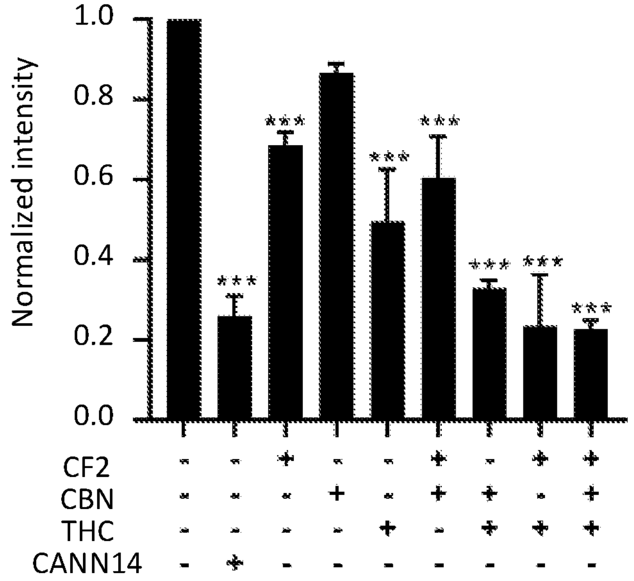
Figure 7B:
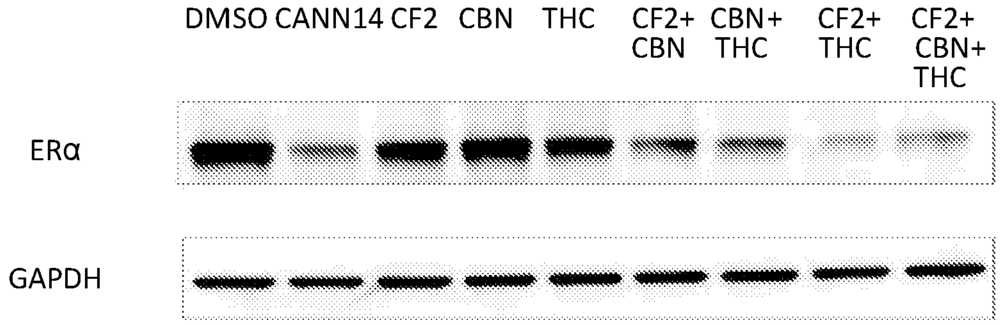
Figure 7G:
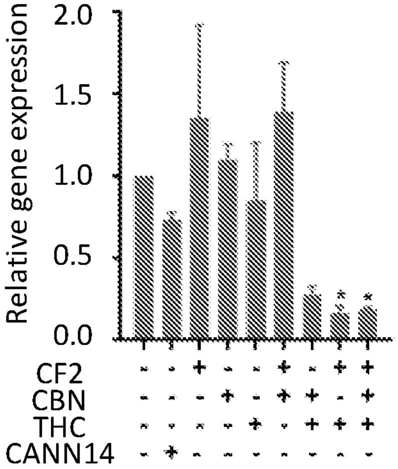
Figure 7H:
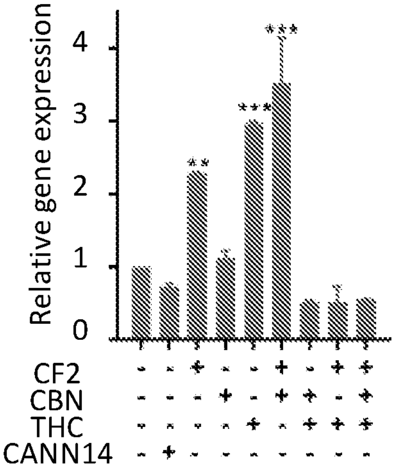
Figure 8A:
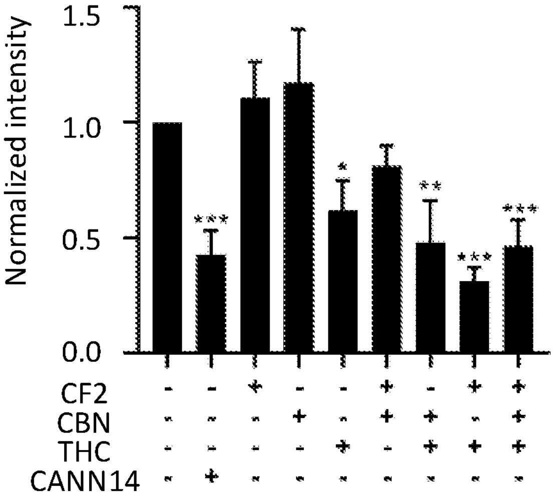
FIGS. 8A-8B show that THC and CF2 reduce ERα protein level. (8A) Normalized intensity (treatment/control) of ERα expression levels of T47D cells that were treated with DMSO control, CANN14, CF2, CBN, THC, or combinations thereof for 18 hours. (8B) A representative western blot of ERα expression in T47D cells that were treated with DMSO control, CANN14, CF2, CBN, THC, or combinations thereof for 18 hours using GAPDH as the loading control.
Figure 8B:
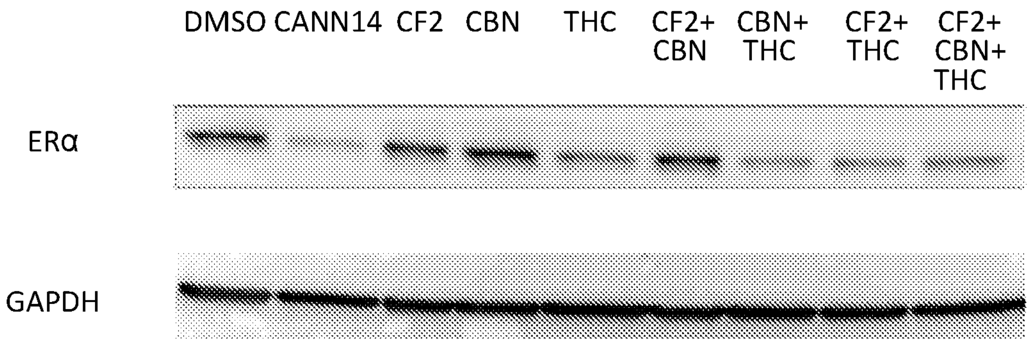
Figure 9A:
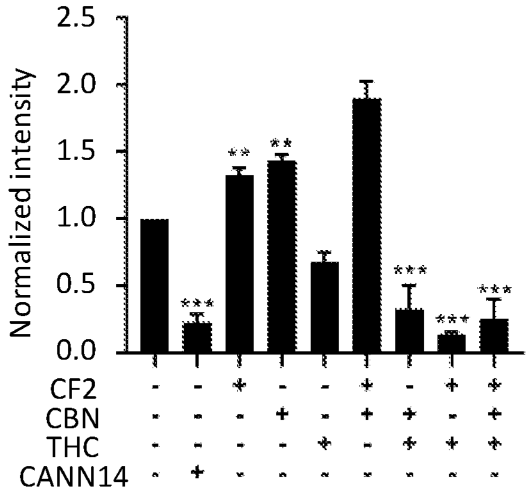
FIGS. 9A-9B show that THC and CF2 reduce ERα protein level. (9A) Normalized intensity (treatment/control) of ERα expression levels of ZR-75-1 cells that were treated with DMSO control, CANN14, CF2, CBN, THC, or combinations thereof for 18 hours. (9B) A representative western blot of ERα expression in ZR-75-1 cells that were treated with DMSO control, CANN14, CF2, CBN, THC, or combinations thereof for 18 hours using GAPDH as the loading control.
Figure 9B:
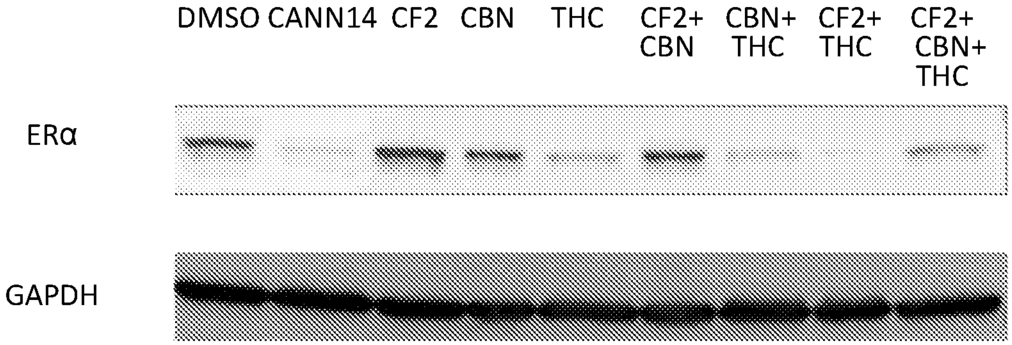

The expression level of ESR1, the gene encoding for ERα, using real-time PCR following 18 hours of CANN14 treatment was examined. RNA was extracted from $5\times10^5$ cells and isolated using TRI reagents (Sigma, UK) according to the manufacturer's protocol. The RNA was reverse transcribed with Maxima First Strand cDNA synthesis kit (Life Technologies, Burlington, Canada) and RT-qPCR was preformed using Taq-Man (Life Technologies Ltd, UK). The fold change of calculated compared to the housekeeping gene 18S, using the formula $2^{(-\Delta\Delta CT)}$ DMSO was used as a control. The expression level of ESR1 was found to significantly reduce due to exposure to CANN14 (FIG. 6G). The activity of ERα as a transcriptional regulator by assessing its binding to Estrogen Response Elements (ERE) following CANN14 treatment was then examined. MCF7 cells were transfected with ERE-luciferase plasmid and luciferase activity was measured. Following 18 hours of CANN14 treatment (4 μg/ml), ERα activity was significantly reduced compared to DMSO control (FIG. 6H). The expression level of AR, CDC25, GREB1, PGR and TFF1; all genes known to be upregulated by estradiol binding to ERα, using real-time PCR was further tested (FIGS. 6I-6M). Following 18 hours of CANN14 treatment, the expression level of all genes was significantly reduced compared to DMSO control.

Figure 10A:
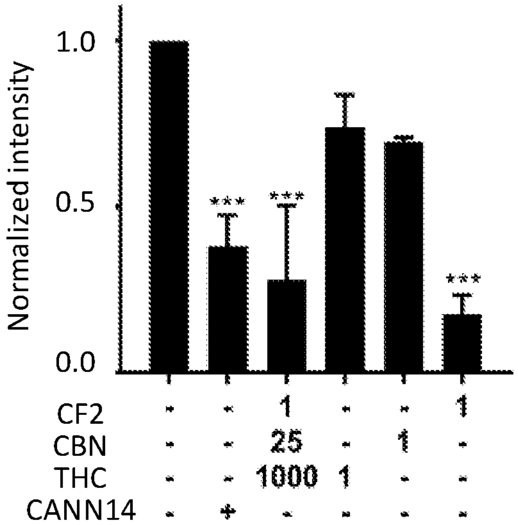
FIGS. 10A-10H show that CF2 reduces ERα protein level. (10A) Normalized intensity (treatment/control) of ERα expression levels of MCF7 cells that were treated with DMSO control, CANN14, CF2, CBN, THC, or a combination thereof at a 1:25:1,000 ratio for 18 hours. (10B) A representative western blot of ERα expression in MCF7 cells that were treated with DMSO control, CANN14, CF2, CBN, THC, or a combination thereof at a 1:25:1,000 ratio for 18 hours using GAPDH as the loading control. (10C) Expression levels of ESR1 gene in MCF7 cells that were incubated with DMSO control, CANN14, CF2, CBN, THC, or a combination thereof at a 1:25:1,000 ratio for 18 hours via real-time PCR. (10D) Expression levels of AR gene in MCF7 cells that were incubated with DMSO control, CANN14, CF2, CBN, THC, or a combination thereof at a 1:25:1,000 ratio for 18 hours via real-time PCR. (10E) Expression levels of CDC25A gene in MCF7 cells that were incubated with DMSO control, CANN14, CF2, CBN, THC, or a combination thereof at a 1:25:1,000 ratio for 18 hours via real-time PCR. (10F) Expression levels of GREB1 gene in MCF7 cells that were incubated with DMSO control, CANN14, CF2, CBN, THC, or a combination thereof at a 1:25:1,000 ratio for 18 hours via real-time PCR. (10G) Expression levels of PGR gene in MCF7 cells that were incubated with DMSO control, CANN14, CF2, CBN, THC, or a combination thereof at a 1:25:1,000 ratio for 18 hours via real-time PCR. (10H) Expression levels of TFF1 gene in MCF7 cells that were incubated with DMSO control, CANN14, CF2, CBN, THC, or a combination thereof at a 1:25:1,000 ratio for 18 hours via real-time PCR. Data are presented as mean±S.E.M (n=3) and statistically analyzed by one-way ANOVA (* $p<0.05$,  $p<0.005$, * $p<0.0001$).
Figure 10B:
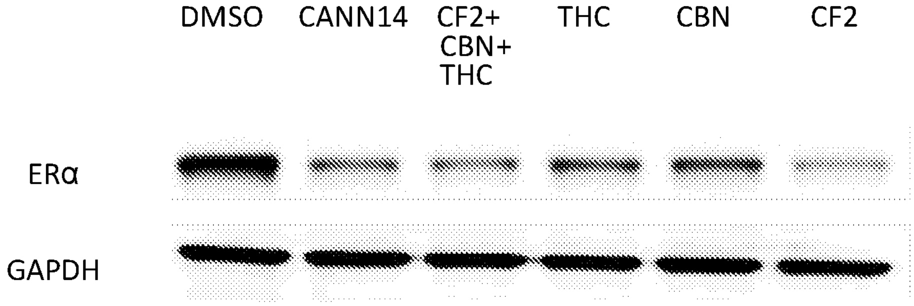
Figure 10C:
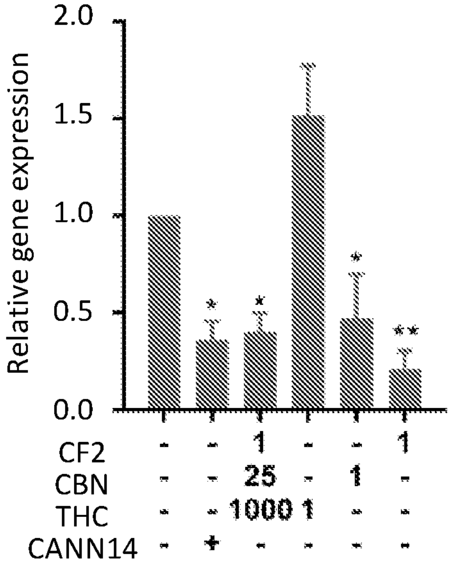
Figure 10D:
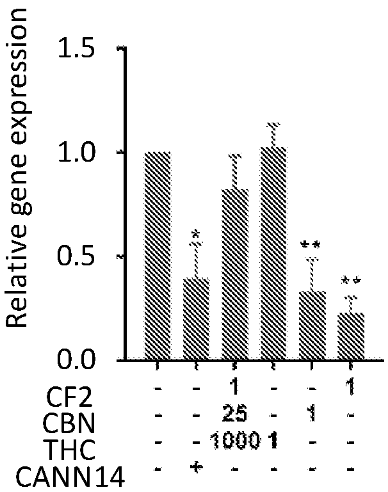
Figure 10E:
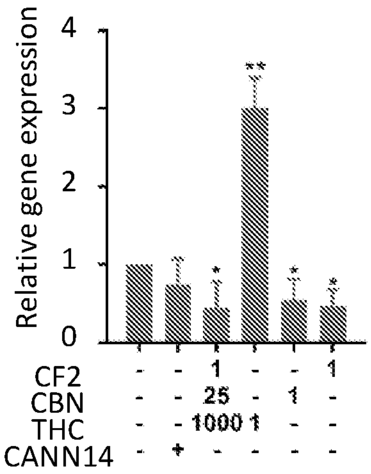
Figure 10F:
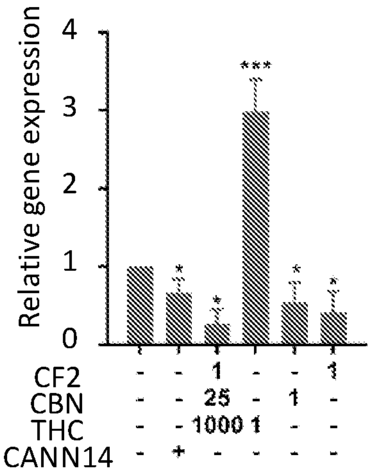
Figure 10G:
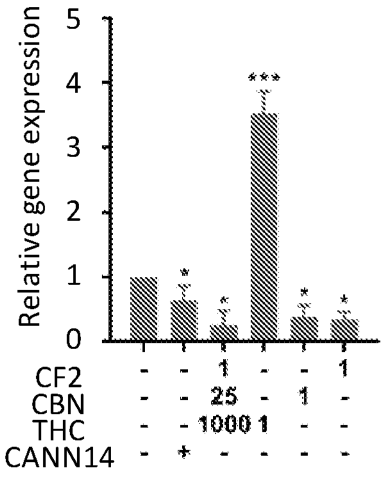
Figure 10H:
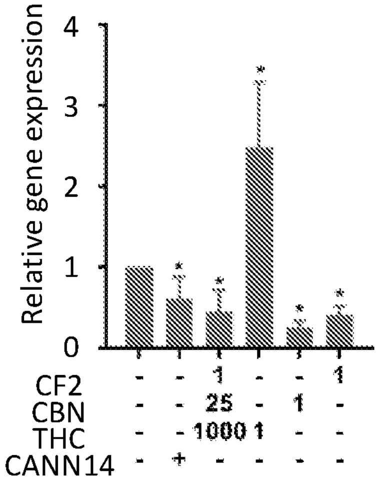

Next, the effect of the three identified cannabinoids on ERα expression and activity was examined. ERα protein level in MCF7, T47D, and ZR-75-1 cells was measured following 18 hours treatment with either THC, CBN or CF2, separately or in combinations (FIGS. 7A-7B, 8A-8B, and 9A-9B, respectively). The combinations of all three molecules or of just THC and CF2 were as effective as the whole extract in reducing the level of ERα protein. The expression level of ESR1, AR, CDC25, GREB1, PGR and TFF1 (genes known to be up-regulated by estradiol binding to ERα) using real-time PCR was further tested (FIGS. 7C-7H). Following 18 hours of treatment with either the combination of all three molecules, THC and CF2, or THC and CBN, the expression levels of most of the examined genes, were significantly reduced. In addition, ERα protein level was significantly reduced the most following treatment with CF2 alone (FIGS. 10A-10B). ESR1 expression level was lowest following treatment with CF2 alone (FIG. 10C). The expression levels of ERα target genes were reduced to the lowest level compared to the control following treatment with CBN or CF2 separately (FIGS. 10D-10H).

Example 4

Effects of CF2 in an Endometriosis Model

Figure 11A:
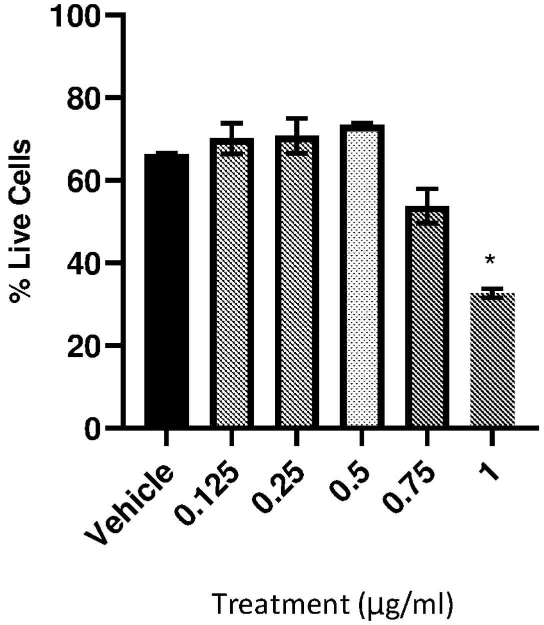
FIGS. 11A-11B show that CF2 reduces cell viability and ERα protein level in Immortalized Human Endometriotic Cell Line (12Z). (11A) % Live cells of 12Z cells that were exposed to vehicle or CF2 at various concentrations. (11B) A representative western blot of ER in 12Z cell line following treatment with vehicle or CF2 using GAPDH as the loading control. Data are presented as mean±S.E.M (n=3) and statistically analyzed by one-way ANOVA (* $p<0.05$,  $p<0.005$, * $p<0.0001$).
Figure 11B:
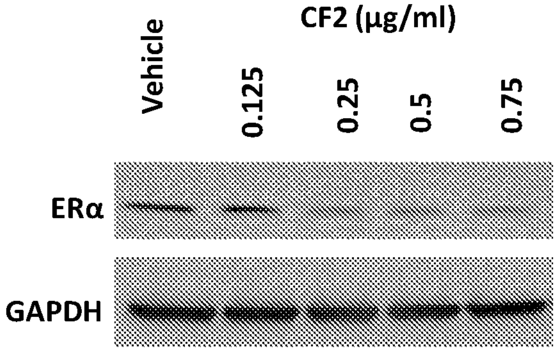

To determine the therapeutic effects of CF2 on endometriosis, an Immortalized Human Endometriotic Cell Line (12Z) was used. Cells were incubated in a 12 well plate, each containing $1\times10^6$ cells. The cells were treated with either vehicle, or CF2 (0.125 to 1 μg/mL each) for 24 hours. Apoptosis was assessed using the Annexin V assay as detailed above. Data are presented as mean±S.E.M (n=3) and statistically analyzed by two-way ANOVA (*$p<0.05$, **$p<0.0001$). FIG. 11A shows a statistically significant reduction in cell viability at a CF2 concentration of 1 μg/mL. FIG. 11**B shows a representative blot of estrogen receptor in 12Z cell line following 5 h treatment with vehicle or CF2 at concentrations of 0.125 to 0.75 μg/mL with GAPDH as the loading control. ERα protein level was significantly reduced following treatment with CF2.

Although the invention has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims.

The invention claimed is:

1. A pharmaceutical cannabinoid composition comprising a compound having a structure represented by Formula II:

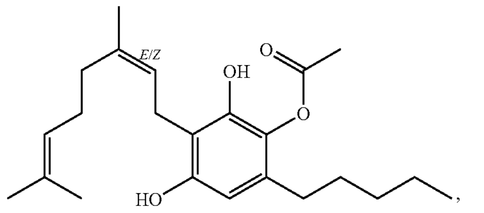

or a pharmaceutically acceptable salt thereof, and a pharmaceutically acceptable carrier.

2. The pharmaceutical cannabinoid composition of claim 1, comprising the compound having a structure represented by Formula II or a pharmaceutically acceptable salt thereof as the sole cannabinoid in said composition.

3. The pharmaceutical cannabinoid composition of claim 1, further comprising at least one additional cannabinoid.

4. The pharmaceutical cannabinoid composition of claim 3, wherein the at least one additional cannabinoid is THC, CBN, or both.

5. The pharmaceutical cannabinoid composition of claim 4, comprising a compound having a structure represented by Formula II or a pharmaceutically acceptable salt thereof and THC; or comprising a compound having a structure represented by Formula II or a pharmaceutically acceptable salt thereof and THC in a weight per weight (w/w) ratio ranging from 1:10 to 1:1,500.

6. The pharmaceutical cannabinoid composition of claim 4, comprising a compound having a structure represented by Formula II or a pharmaceutically acceptable salt thereof and CBN; or comprising a compound having a structure represented by Formula II or a pharmaceutically acceptable salt thereof and CBN in a weight per weight (w/w) ratio ranging from 1:1 to 1:40.

7. The pharmaceutical cannabinoid composition of claim 4, comprising a compound having a structure represented by Formula II or a pharmaceutically acceptable salt thereof, CBN, and THC, wherein the CBN and THC are present in said pharmaceutical composition in a weight per weight (w/w) ratio ranging from 1:5 to 1:100; or comprising a compound having a structure represented by Formula II or a pharmaceutically acceptable salt thereof, CBN and THC in a weight per weight (w/w) ratio ranging from 1:1:10 to 1:30:1,500.

8. A pharmaceutical combination comprising:

a. at least one cannabinoid comprising a compound having a structure represented by Formula II

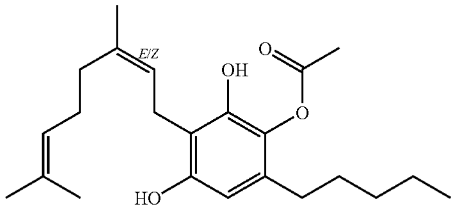

or a pharmaceutically acceptable salt thereof; and b. at least one ER activation inhibitor comprising a selective ER modulator (SERM).

9. The pharmaceutical combination of claim 8, wherein the SERM is tamoxifen.

10. The pharmaceutical combination of claim 8, further comprising at least one additional cannabinoid.

11. The pharmaceutical combination of claim 10, wherein the at least one additional cannabinoid comprises THC, CBN, or both.

12. A method for treating a subject afflicted with an ER-related cell-proliferative disease, the method comprising administering to said subject a therapeutically effective amount of the pharmaceutical cannabinoid composition of claim 1.

13. The method of claim 12, wherein the ER-related cell-proliferative disease is breast cancer.

14. The method of claim 12, wherein the pharmaceutical composition further comprises at least one additional cannabinoid.

15. The method of claim 14, wherein the at least one additional cannabinoid comprises THC, CBN, or both.

16. A method of increasing or enhancing the therapeutic efficacy of an ER activation inhibitor comprising a selective ER modulator (SERM) in a subject in need thereof, the method comprising co-administering to said subject a therapeutically effective amount of the pharmaceutical cannabinoid composition of claim 1 and the SERM.

17. The method of claim 16, wherein said subject is characterized by being resistant or non-responsive to the ER activation inhibitor.

18. The method of claim 16, further comprising a step preceding said co-administering, wherein the step comprises selecting a subject resistant or non-responsive to the ER activation inhibitor by determining responsiveness of a biological sample obtained or derived from said subject to the ER activation inhibitor, wherein low or lack of response of said biological sample to said ER activation inhibitor, compared to a control, is indicative of said subject being suitable for treatment by co-administering said pharmaceutical composition and the ER activation inhibitor.

19. The method of claim 16, wherein the pharmaceutical composition further comprises at least one additional cannabinoid.

20. The method of claim 19, wherein the at least one additional cannabinoid comprises THC, CBN, or both.

* * * * *